(12) United States Patent
Dellinger

(10) Patent No.: US 11,389,460 B2
(45) Date of Patent: Jul. 19, 2022

(54) METHODS AND COMPOSITIONS FOR TREATING ENDOMETRIAL CANCER

(71) Applicant: City of Hope, Duarte, CA (US)

(72) Inventor: Thanh Dellinger, Azusa, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/131,985

(22) Filed: Sep. 14, 2018

(65) Prior Publication Data

US 2019/0083510 A1    Mar. 21, 2019

Related U.S. Application Data

(60) Provisional application No. 62/559,294, filed on Sep. 15, 2017.

(51) Int. Cl.
| | | |
|---|---|---|
| *A61K 31/57* | (2006.01) | |
| *A61P 35/00* | (2006.01) | |
| *A61K 31/09* | (2006.01) | |
| *A61K 9/00* | (2006.01) | |
| *A61K 9/20* | (2006.01) | |
| *A61K 9/10* | (2006.01) | |
| *A61K 9/48* | (2006.01) | |
| *A61K 9/08* | (2006.01) | |

(52) U.S. Cl.
CPC ............ *A61K 31/57* (2013.01); *A61K 9/0053* (2013.01); *A61K 9/0095* (2013.01); *A61K 9/08* (2013.01); *A61K 9/10* (2013.01); *A61K 9/2004* (2013.01); *A61K 9/48* (2013.01); *A61K 31/09* (2013.01); *A61P 35/00* (2018.01)

(58) Field of Classification Search
CPC .......... A61K 31/09; A61K 31/57; A61P 35/00
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,362,720 A * | 11/1994 | Labrie .................. | A61K 9/1647 514/169 |
| 5,403,841 A | 4/1995 | Lang et al. | |
| 8,664,276 B2 | 3/2014 | Watt et al. | |
| 8,980,954 B2 | 3/2015 | Vander Jagt et al. | |
| 2011/0136751 A1 | 6/2011 | Estrela et al. | |
| 2011/0189275 A1 | 8/2011 | Schultheiss et al. | |

FOREIGN PATENT DOCUMENTS

| | | |
|---|---|---|
| EP | 2698155 A1 | 2/2014 |
| WO | WO-2017/088058 A1 | 6/2017 |

OTHER PUBLICATIONS

Lowe et al. Oct. 2014 vol. 74, Issue 19 Supplement, Cancer Chemistry, AACR Annual Meeting. (Year: 2014).*

Aghajanian, C. et al. (Jun. 1, 2011, Epub May 2, 2011.). "Phase II trial of bevacizumab in recurrent or persistent endometrial cancer: a Gynecologic Oncology Group study," *J Clin Oncol* 29(16):2259-2265.

Al-Muhammed, J. et al. (May-Jun. 1996). "In-vivo studies on dexamethasone sodium phosphate liposomes," *J Microencapsul* 13(3):293-306.

Altschul, S.F. et al. (Oct. 5, 1990). "Basic local alignment search tool," *J Mol Biol* 215(3):403-10.

Altschul, S.F. et al. (Sep. 1997). "Gapped BLAST and PSI-BLAST: a new generation of protein database search programs," Nuc. Acids Res. 25(17):3389-3402.

Berge, S.M. et al. (Jan. 1977). "Pharmaceutical salts," J Pharm Sci 66(1):1-19.

Bradford, L. S., Rauh-Hain, J. A., Schorge, J., Birrer, M. J. & Dizon, D. S. Advances in the management of recurrent endometrial cancer. *American journal of clinical oncology* 38, 206-212, doi:10.1097/COC.0b013e31829a2974 (2015).

Burke, W. M. et al. Endometrial cancer: A review and current management strategies: Part I. *Gynecologic Oncology* 134, 385-392, doi:http://doi.org/10.1016/j.ygyno.2014.05.018 (2014).

Burke, W. M. et al. Endometrial cancer: A review and current management strategies: Part II. *Gynecologic Oncology* 134, 393-402, doi:http://doi.org/10.1016/j.ygyno.2014.06.003 (2014).

Chonn, A. et al. (Dec. 1995). "Recent advances in liposomal drug-delivery systems," *Curr Opin Biotechnol* 6(6):698-708.

Dizon, D.S. et al. (Jun. 2014). "Advances in the diagnosis and treatment of uterine sarcomas," *Discovery Medicine* 17(96):339-345.

Eyles, J.E. et al. (Jul. 1997). "Oral delivery and fate of poly(lactic acid) microsphere-encapsulated interferon in rats," J. Pharm. Pharmacol. 49(7):669-674.

Gao, Z.H. et al. (Jun. 1995). "Controlled release of a contraceptive steroid from biodegradable and injectable gel formulations: in vitro evaluation," Pharm. Res 12(6):857-863.

Henikoff, S. et al. (Nov. 15, 1992). "Amino acid substitution matrices from protein blocks," *PNAS USA* 89(22):10915-10919.

Lheureux, S. & Oza, A. M. Endometrial cancer—targeted therapies myth or reality? Review of current targeted treatments. *European Journal of Cancer* 59, 99-108, doi:https://doi.org/10.1016/j.ejca.2016.02.016 (2016).

Morice, P. et al. (Mar. 12, 2016, e-published Sep. 6, 2015.). "Endometrial cancer," *Lancet* 38:1094-1108.

Needleman, S.B. (Mar. 1970). "A general method applicable to the search for similarities in the amino acid sequence of two proteins," *J. Mol. Biol.* 48:443.

Ostro, M.J. et al. (Aug. 1989). "Use of liposomes as injectable-drug delivery systems," *Am J Hosp Pharm* 46(8):1576-1587.

Oza, A.M. et al. (Aug. 20, 2011, e-published Jul. 25, 2011). "Phase II study of temsirolimus in women with recurrent or metastatic endometrial cancer: a trial of the NCIC Clinical Trials Group," Journal of Clinical Oncology: 29(24):3278-3285.

Pearson, W.R. et al. (Apr. 1998). "Improved tools for biological sequence comparison," 85(8):2444-2448.

(Continued)

*Primary Examiner* — Kara R McMillian

(74) *Attorney, Agent, or Firm* — Mintz, Levin, Cohn, Ferris, Glovsky and Popeo, P.C.

(57) ABSTRACT

Provided herein are, inter alia, methods and compositions for treating cancer in a subject in need thereof comprising a therapeutically effective amount of a stilbenoid compound and a progestin.

18 Claims, 6 Drawing Sheets

(56) References Cited

OTHER PUBLICATIONS

Pecorelli, S. (May 2009). "Revised FIGO staging for carcinoma of the vulva, cervix, and endometrium," *Int J. Gynaecol Obstet* 105(2):103-4.
Rao. K.P. (1995). "Recent developments of collagen-based materials for medical applications and drug delivery systems" *J. Biomater Sci. Polym. Ed.* 7(7):623-645.
Siegel, R.L. et al. (Jan.-Feb. 2016 Epub Jan. 7, 2016). "Cancer statistics, 2016, *CA: A Cancer Journal of Clinicians*," 66:7-30.
Singh, M. et al. (Aug. 2007, e-published May 25, 2007). "Relationship of estrogen and progesterone receptors to clinical outcome in metastatic endometrial carcinoma: a Gynecologic Oncology Group Study," *Gynecol Oncol* 106(2):325-333.
Smith, T.F. et al. (1981). "Comparison of Biosequences," *Adv. Appl. Math.* 2(4)482-489.
Wang, Y.L. et al. (Oct. 2017, e-published May 29, 2017). "Pterostilbene suppresses human endometrial cancer cells in vitro by down-regulating miR-663b," *Acta Pharmacologica Sinica* 38(10):1394-1400.
Myers, A. P. et al. Tumor mutational analysis of GOG248, a phase II study of temsirolimus or temsirolimus and alternating megestrol acetate and tamoxifen for advanced endometrial cancer (EC): An NRG Oncology/Gynecologic Oncology Group study. *Gynecologic Oncology* 141, 43-48, doi:10.1016/j.ygyno.2016.02.025 (2016).
DeLeon, M. C., Ammakkanavar, N. R. & Matei, D. Adjuvant therapy for endometrial cancer. *Journal of Gynecologic Oncology* 25, 136-147, doi:10.3802/jgo.2014.25.2.136 (2014).
Hansen, J. et al. The effect of weight-based chemotherapy dosing in a cohort of gynecologic oncology patients. *Gynecologic Oncology* 138, 154-158, doi:https://doi.org/10.1016/j.ygyno.2015.04.040 (2015).
Lentz, S. S., Brady, M. F., Major, F. J., Reid, G. C. & Soper, J. T. High-dose megestrol acetate in advanced or recurrent endometrial carcinoma: a Gynecologic Oncology Group Study. Journal of clinical oncology : official journal of the American Society of Clinical Oncology 14, 357-361, doi:10.1200/jco.1996.14.2.357 (1996).
Rauh-Hain, J. A. & del Carmen, M. G. Treatment for Advanced and Recurrent Endometrial Carcinoma: Combined Modalities. *The Oncologist* 15, 852-861, doi:10.1634/theoncologist.2010-0091 (2010).
Lee, W. L. et al. Hormone therapy for patients with advanced or recurrent endometrial cancer. *Journal of the Chinese Medical Association: JCMA* 77, 221-226, doi:10.1016/j.jcma.2014.02.007 (2014).
Yang, S., Thiel, K. W., De Geest, K. & Leslie, K. K. Endometrial cancer: reviving progesterone therapy in the molecular age. *Discovery medicine* 12, 205-212 (2011).
Kong, Y. et al. Pterostilbene induces apoptosis and cell cycle arrest in diffuse large B-cell lymphoma cells. Scientific reports 6, 37417, doi:10.1038/srep37417 (2016).
Lee, H., Kim, Y., Jeong, J. H., Ryu, J.-H. & Kim, W.-Y. ATM/CHK/p53 Pathway Dependent Chemopreventive and Therapeutic Activity on Lung Cancer by Pterostilbene. PLoS ONE 11, e0162335, doi:10.1371/journal.pone.0162335 (2016).
Dhar, S. et al. Dietary pterostilbene is a novel MTA1-targeted chemopreventive and therapeutic agent in prostate cancer. Oncotarget 7, 18469-18484, doi:10.18632/oncotarget.7841 (2016).
Nikhil, K., Sharan, S., Singh, A. K., Chakraborty, A. & Roy, P. Anticancer Activities of Pterostilbene-Isothiocyanate Conjugate in Breast Cancer Cells: Involvement of PPARγ. *PLoS ONE* 9, e104592, doi:10.1371/journal.pone.0104592 (2014).
Li, K. et al. Pterostilbene Acts through Metastasis-Associated Protein 1 to Inhibit Tumor Growth, Progression and Metastasis in Prostate Cancer. PLoS ONE 8, e57542, doi:10.1371/journal.pone.0057542 (2013).
Paul, S. et al. Anti-inflammatory action of pterostilbene is mediated through the p38 MAPK pathway in colon cancer cells. *Cancer prevention research (Philadelphia, Pa.)* 2, 650-657, doi: 10.1158/1940-6207.capr-08-0224 (2009).
Pan, M.-H. et al. Pterostilbene inhibited tumor invasion via suppressing multiple signal transduction pathways in human hepatocellular carcinoma cells. *Carcinogenesis* 30, 1234-1242, doi:10.1093/carcin/bgp121 (2009).
Suh, N. et al. Pterostilbene, an Active Constituent of Blueberries, Suppresses Aberrant Crypt Foci Formation in the Azoxymethane-Induced Colon Carcinogenesis Model in Rats. Clinical Cancer Research 13, 350 (2007).
Hsiao, P. C. et al. Pterostilbene simultaneously induced G0/G1-phase arrest and MAPK-mediated mitochondrial-derived apoptosis in human acute myeloid leukemia cell lines. PLoS ONE 9, e105342, doi:10.1371/journal.pone.0105342 (2014).
Priego, S. et al. Natural polyphenols facilitate elimination of HT-29 colorectal cancer xenografts by chemoradiotherapy: a Bcl-2- and superoxide dismutase 2-dependent mechanism. *Molecular Cancer Therapeutics* 7, 3330-3342, doi:10.1158/1535-7163.mct-08-0363 (2008).
Xie, B. et al. Pterostilbene Inhibits Human Multiple Myeloma Cells via ERK1/2 and JNK Pathway In Vitro and In Vivo. *International Journal of Molecular Sciences* 17, 1927, doi: 10.3390/ijms17111927 (2016).
Schmidt, L. et al. Case-specific potentiation of glioblastoma drugs by pterostilbene. Oncotarget 7, 73200-73215, doi:10.18632/oncotarget.12298 (2016).
Estrela, J. M., Ortega, A., Mena, S., Rodriguez, M. L. & Asensi, M. Pterostilbene: Biomedical applications. Critical reviews in clinical laboratory sciences 50, 65-78, doi:10.3109/10408363.2013.805182 (2013).
Pan, C. et al. Estrogen receptor-alpha36 is involved in pterostilbene-induced apoptosis and anti-proliferation in in vitro and in vivo breast cancer. PloS one 9, e104459, doi:10.1371/journal.pone.0104459 (2014).
Chen, R. J., Ho, C. T. & Wang, Y. J. Pterostilbene induces autophagy and apoptosis in sensitive and chemoresistant human bladder cancer cells. *Molecular nutrition & food research* 54, 1819-1832, doi:10.1002/mnfr.201000067 (2010).
Schneider, J. G., Alosi, J. A., McDonald, D. E. & McFadden, D. W. Pterostilbene inhibits lung cancer through induction of apoptosis. The Journal of surgical research 161, 18-22, doi:10.1016/j.jss.2009.06.027 (2010).
Tolba, M. F. & Abdel-Rahman, S. Z. Pterostilbine, an active component of blueberries, sensitizes colon cancer cells to 5-fluorouracil cytotoxicity. Scientific reports 5, 15239, doi:10.1038/srep15239 (2015).
Kuramoto, H. Studies of the growth and cytogenetic properties of human endometrial adenocarcinoma in culture and its development into an established line. Acta obstetrica et gynaecologica Japonica 19, 47-58 (1972).
Mo, B. et al. ECC-1 cells: a well-differentiated steroid-responsive endometrial cell line with characteristics of luminal epithelium. Biology of reproduction 75, 387-394, doi:10.1095/biolreprod.106.051870 (2006).
Zhang, L. et al. Nongenomic effect of estrogen on the MAPK signaling pathway and calcium influx in endometrial carcinoma cells. *J Cell Biochem* 106, 553-562, doi:10.1002/jcb.22017 (2009).
Chou, T. C. Drug combination studies and their synergy quantification using the Chou-Talalay method. Cancer research 70, 440-446, doi:10.1158/0008-5472.CAN-09-1947 (2010).
Kosuru, R., Rai, U., Prakash, S., Singh, A. & Singh, S. Promising therapeutic potential of pterostilbene and its mechanistic insight based on preclinical evidence. European journal of pharmacology 789, 229-243, doi:10.1016/j.ejphar.2016.07.046 (2016).
Mannal, P., McDonald, D. & McFadden, D. Pterostilbene and tamoxifen show an additive effect against breast cancer in vitro. *American journal of surgery* 200, 577-580, doi:10.1016/j.amjsurg.2010.07.022 (2010).
Mannal, P. W., Alosi, J. A., Schneider, J. G., McDonald, D. E. & McFadden, D. W. Pterostilbene inhibits pancreatic cancer in vitro. *Journal of gastrointestinal surgery: official journal of the Society for Surgery of the Alimentary Tract* 14, 873-879, doi:10.1007/s11605-010-1164-4 (2010).

(56) References Cited

OTHER PUBLICATIONS

Gehm, B. D., McAndrews, J. M., Chien, P. Y. & Jameson, J. L. Resveratrol, a polyphenolic compound found in grapes and wine, is an agonist for the estrogen receptor. Proceedings of the National Academy of Sciences of the United States of America 94, 14138-14143 (1997).

Bowers, J. L., Tyulmenkov, V. V., Jernigan, S. C. & Klinge, C. M. Resveratrol acts as a mixed agonist/antagonist for estrogen receptors alpha and beta. Endocrinology 141, 3657-3667, doi:10.1210/endo.141.10.7721 (2000).

Bhat, K. P. et al. Estrogenic and antiestrogenic properties of resveratrol in mammary tumor models. Cancer Res 61, 7456-7463 (2001).

Robb, E. L. & Stuart, J. A. The stilbenes resveratrol, pterostilbene and piceid affect growth and stress resistance in mammalian cells via a mechanism requiring estrogen receptor beta and the induction of Mn-superoxide dismutase. Phytochemistry 98, 164-173, doi:10.1016/j.phytochem.2013.11.019 (2014).

Kala, R. & Tollefsbol, T. O. A Novel Combinatorial Epigenetic Therapy Using Resveratrol and Pterostilbene for Restoring Estrogen Receptor-α (ERα) Expression in ERα-Negative Breast Cancer Cells. PLoS ONE 11, e0155057, doi:10.1371/journal.pone.0155057 (2016).

Bjornstrom, L. & Sjoberg, M. Estrogen receptor-dependent activation of AP-1 via non-genomic signalling. Nuclear receptor 2, 3, doi:10.1186/1478-1336-2-3 (2004).

Kim, J. J., Kurita, T. & Bulun, S. E. Progesterone Action in Endometrial Cancer, Endometriosis, Uterine Fibroids, and Breast Cancer. Endocrine Reviews 34, 130-162, doi:10.1210/er.2012-1043 (2013).

Dai, D., Wolf, D. M., Litman, E. S., White, M. J. & Leslie, K. K. Progesterone Inhibits Human Endometrial Cancer Cell Growth and Invasiveness. Cancer Research 62, 881 (2002).

Zhang, K. & Chow, P. K. The effect of megestrol acetate on growth of HepG2 cells in vitro and in vivo. Clin Cancer Res 10, 5226-5232, doi:10.1158/1078-0432.CCR-04-0061 (2004).

Ruiz, M. J. et al. Dietary administration of high doses of pterostilbene and quercetin to mice is not toxic. Journal of agricultural and food chemistry 57, 3180-3186, doi:10.1021/jf803579e (2009).

Riche, D. M. et al. Analysis of safety from a human clinical trial with pterostilbene. Journal of toxicology 2013, 463595, doi:10.1155/2013/463595 (2013).

Yang, T. T., Sinai, P. & Kain, S. R. An acid phosphatase assay for quantifying the growth of adherent and nonadherent cells. Analytical biochemistry 241, 103-108, doi:10.1006/abio.1996.0383 (1996).

Wen, W. et al. Synergistic anti-tumor effect of combined inhibition of EGFR and JAK/STAT3 pathways in human ovarian cancer. Molecular cancer 14, 100, doi:10.1186/s12943-015-0366-5 (2015).

Wen, W. et al. Targeting JAK1/STAT3 signaling suppresses tumor progression and metastasis in a peritoneal model of human ovarian cancer. Molecular cancer therapeutics 13, 3037-3048, doi:10.1158/1535-7163.MCT-14-0077 (2014).

Lu, J. et al. Novel angiogenesis inhibitory activity in cinnamon extract blocks VEGFR2 kinase and downstream signaling. Carcinogenesis 31, 481-488, doi:10.1093/carcin/bgp292 (2010).

NCBI Accession No. NM_000077.4, Oct. 21, 2018, 6 pages.
NCBI Accession No. NM_000125.3, Nov. 18, 2018, 7 pages.
NCBI Accession No. NM_000141.4, Dec. 2, 2018, 8 pages.
NCBI Accession No. NM_000249.3, Nov. 18, 2018, 5 pages.
NCBI Accession No. NM_000314.6, Nov. 18, 2018, 9 pages.
NCBI Accession No. NM_000546.5, Dec. 2, 2018, 10 pages.
NCBI Accession No. NM_000926.4, Dec. 9, 2018, 8 pages.
NCBI Accession No. NM_001040275.1, Nov. 24, 2018, 5 pages.
NCBI Accession No. NM_001098209.1, Nov. 25, 2018, 8 pages.
NCBI Accession No. NM_001202474.3, Nov. 18, 2018, 6 pages.
NCBI Accession No. NM_001238.3, Oct. 21, 2018, 4 pages.
NCBI Accession No. NM_001271161.2, Nov. 18, 2018, 6 pages.
NCBI Accession No. NM_001271162.1, Nov. 18, 2018, 6 pages.
NCBI Accession No. NM_001318536.1, Oct. 13, 2018, 3 pages.
NCBI Accession No. NM_001323303.1, Dec. 5, 2018, 5 pages.
NCBI Accession No. NM_004448.3, Dec. 2, 2018, 8 pages.
NCBI Accession No. NM_006015.5, Oct. 14, 2018, 10 pages.
NCBI Accession No. NM_006218.3, Nov. 18, 2018, 7 pages.
NCBI Accession No. NM_007182.4, Nov. 18, 2018, 4 pages.
NCBI Accession No. NM_014225.5, Oct. 21, 2018, 5 pages.
NCBI Accession No. NM_033360.3, Dec. 4, 2018, 7 pages.
NCBI Accession No. NM_053056.2, Dec. 2, 2018, 5 pages.
NCBI Accession No. NM_181523.2, Oct. 20, 2018, 7 pages.
NCBI Accession No. NP_000068.1, Oct. 21, 2018, 4 pages.
NCBI Accession No. NP_000116.2, Nov. 18, 2018, 4 pages.
NCBI Accession No. NP_000132.3, Dec. 2, 2018, 5 pages.
NCBI Accession No. NP_000240.1, Nov. 18, 2018, 3 pages.
NCBI Accession No. NP_000305.3, Nov. 21, 2018, 4 pages.
NCBI Accession No. NP_000537.3, Dec. 2, 2018, 7 pages.
NCBI Accession No. NP_000917.3, Dec. 9, 2018, 5 pages.
NCBI Accession No. NP_001035365.1, Nov. 24, 2018, 3 pages.
NCBI Accession No. NP_001091679.1, Nov. 25, 2018, 6 pages.
NCBI Accession No. NP_001189403.1, Nov. 18, 2018, 3 pages.
NCBI Accession No. NP_001229.1, Dec. 2, 2018, 3 pages.
NCBI Accession No. NP_001258090.1, Nov. 18, 2018, 3 pages.
NCBI Accession No. NP_001305465.1, Oct. 13, 2018, 3 pages.
NCBI Accession No. NP_001310232.1, Dec. 5, 2018, 4 pages.
NCBI Accession No. NP_004439.2, Dec. 2, 2018, 5 pages.
NCBI Accession No. NP_006006.3, Nov. 22, 2018, 6 pages.
NCBI Accession No. NP_006209.2, Dec. 2, 2018, 4 pages.
NCBI Accession No. NP_009113.3, Nov. 18, 2018, 3 pages.
NCBI Accession No. NP_055040.2, Nov. 22, 2018, 4 pages.
NCBI Accession No. NP_203524.1, Dec. 4, 2018, 4 pages.
NCBI Accession No. NP_444284.1, Dec. 2, 2018, 3 pages.
NCBI Accession No. NP_852664.1, Dec. 2, 2018, 4 pages.

* cited by examiner

METHODS AND COMPOSITIONS FOR TREATING ENDOMETRIAL CANCER

CROSS-REFERENCE

This application claims the benefit of priority to U.S. Provisional Application No. 62/559,294, filed Sep. 15, 2017, which is incorporated herein by reference in its entirety.

GOVERNMENT SUPPORT

This invention was made with government support under Grant No. P30CA033572 awarded by the National Institutes of Health. The government has certain rights in the invention.

BACKGROUND

Endometrial cancer is the most common gynecologic cancer in the United States, and unlike most other cancers, its incidence and mortality has been rising over the past decade[1-3]. While frequently curable in the early stages of this disease, a substantial portion of patients are diagnosed with incurable, advanced stage and recurrent disease. Additionally, endometrial cancer patients are often plagued by comorbidities such as obesity, diabetes mellitus, and hypertension, making novel therapies, which are frequently toxic, challenging to study. Only a few treatment options are available for advanced stage and recurrent endometrial cancer patients, and few novel drugs have been recently tested in clinical trial, with modest response rates[4-12]. One frequently used drug in endometrial cancer patients, especially those with metastatic lung lesions or who are deemed medically unfit for surgical management, is the progestin megestrol acetate, which is associated with a 20-30% response rate in advanced stage/recurrent endometrial cancer patients[13-16].

BRIEF SUMMARY

Provided herein are, inter alia, methods and compositions for treating cancer in a subject in need thereof comprising a therapeutically effective amount of a stilbenoid compound and a progestin.

In an aspect, provided herein is a method of treating cancer in a subject in need thereof, the method including administering to the subject a therapeutically effective amount of (i) pterostilbene or a pharmaceutically acceptable salt thereof; and (ii) megestrol or a pharmaceutically acceptable salt thereof.

In an aspect, provided herein is a method of preventing cancer in a subject who is at risk of cancer, the method including administering to the subject a therapeutically effective amount of (i) pterostilbene or a pharmaceutically acceptable salt thereof; and (ii) megestrol or a pharmaceutically acceptable salt thereof.

In an aspect, provided herein is a method of reducing the likelihood that a subject will develop cancer, the method including administering to the subject a therapeutically effective amount of (i) pterostilbene or a pharmaceutically acceptable salt thereof; and (ii) megestrol or a pharmaceutically acceptable salt thereof.

In an aspect, provided herein is a method of increasing the likelihood that a subject will respond to treatment for cancer comprising megestrol or a pharmaceutically acceptable salt thereof, including administering pterostilbene or a pharmaceutically acceptable salt thereof to the subject.

In an aspect, provided herein is a method of increasing the likelihood that a subject will respond to megestrol acetate treatment for cancer, including administering pterostilbene or a pharmaceutically acceptable salt thereof to the subject.

In an aspect, provided herein is a method of increasing the likelihood that a subject will respond to treatment for cancer comprising pterostilbene or a pharmaceutically acceptable salt thereof, including administering megestrol or a pharmaceutically acceptable salt thereof to the subject.

In an aspect, provided herein is a method of increasing the likelihood that a subject will respond to pterostilbene treatment for cancer, including administering megestrol acetate to the subject.

In an aspect, provided herein is a method of treating cancer in a subject who has previously received a first amount of megestrol or a pharmaceutically acceptable salt thereof, including administering (i) a second amount of megestrol or a pharmaceutically acceptable salt thereof that is less than said first amount; and (ii) an amount of pterostilbene or a pharmaceutically acceptable salt thereof.

In an aspect, provided herein is a method of treating cancer in a subject who has previously received a first amount of megestrol acetate, including administering (i) a second amount of megestrol acetate that is less than said first amount; and (ii) an amount of pterostilbene.

In an aspect, provided herein is a method of treating cancer in a subject who has previously received a first amount of pterostilbene or a pharmaceutically acceptable salt thereof, including administering (i) a second amount of pterostilbene or a pharmaceutically acceptable salt thereof that is less than said first amount; and (ii) an amount of megestrol or a pharmaceutically acceptable salt thereof.

In an aspect, provided herein is a method of treating cancer in a subject who has previously received a first amount of pterostilbene, including administering (i) a second amount of pterostilbene that is less than said first amount; and (ii) an amount of megestrol acetate.

In an aspect, provided herein is a pharmaceutical composition including a therapeutically effective amount of (i) a stilbenoid compound and a progestin, and (ii) a pharmaceutically acceptable excipient.

In an aspect, provided herein is a pharmaceutical composition including a therapeutically effective amount of (i) pterostilbene or a pharmaceutically acceptable salt thereof and megestrol or a pharmaceutically acceptable salt thereof, and (ii) a pharmaceutically acceptable excipient.

In an aspect, provided herein is a method of treating estrogen receptor (ER) positive and/or progesterone receptor (PR) positive cancer in a subject in need thereof, including administering a therapeutically effective amount of pterostilbene or a pharmaceutically acceptable salt thereof to the subject.

BRIEF DESCRIPTION OF THE DRAWINGS

FIG. 2C: HEC-1A cells were treated with Pterostilbene or megestrol acetate alone or in combination at various molar ratios. Cell viability was determined 72 h later.

FIG. 3A: HEC-1A cells were treated with Pterostilbene or megestrol acetate at various concentrations for 24 h. Whole cells were collected and determined for the expression of cell survival molecules and cell cycle molecules by Western blot. FIG. 3B: HEC-1A cells were treated with Pterostilbene (75 µM), megestrol acetate (75 µM) or the combination for 24 h. Whole cell lysates were collected and measured for the change of cell cycle and apoptosis pathways by Western blot.

FIG. 4A: HEC-1A cells were treated with Pterostilbene or megestrol acetate at various concentrations for 24 h. Whole cells were collected and determined for the change of STAT3, AKT and ERK pathways and ER expression by Western blot. FIG. 4B: HEC-1A cells were treated with Pterostilbene (75 µM), megestrol acetate (75 µM) or the combination for 24 h. Whole cell lysates were collected and measured for the change of cell signaling pathways by Western blot.

FIG. 5C: Tumor weight was measured at end of the treatment. Data represent means±SD (n=8-10). **, P<0.005, combination versus vehicle.

DETAILED DESCRIPTION

Definitions

Figure 1:
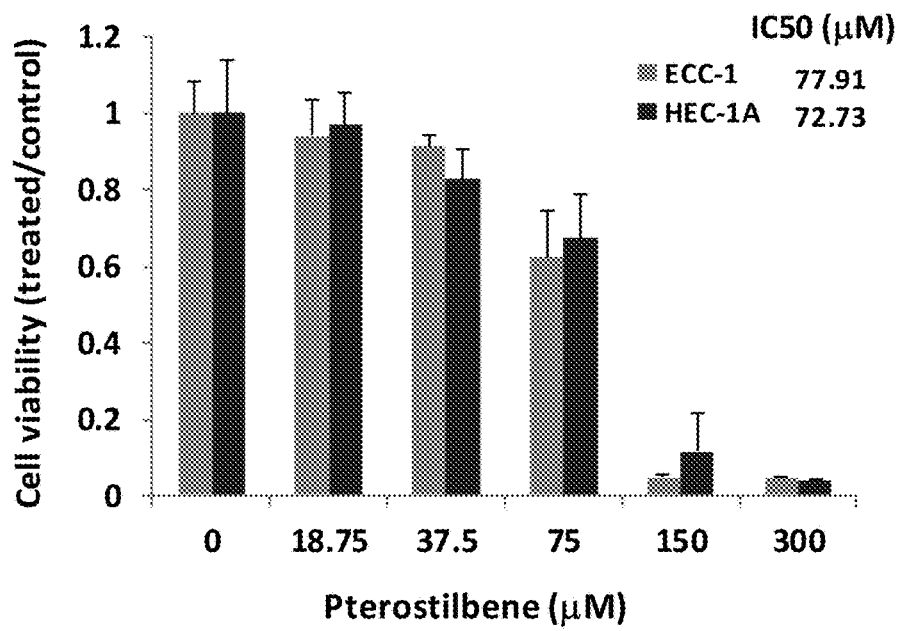
FIG. 1. Pterostilbene (PTE) inhibits endometrial cancer cell viability. Cells were treated with vehicle (DMSO) or Pterostilbene (37.5-300 µM) for 48 hrs. Cell viability was determined using MTS assay. The $IC_{50}$ was determined by the Chou-Talalay method. Data are expressed as the ratio to control treated with vehicle (DMSO).

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention.

The following definitions are provided to facilitate understanding of certain terms used frequently herein and are not meant to limit the scope of the present disclosure.

As used herein, the term "about" in the context of a numerical value or range means±10% of the numerical value or range recited or claimed, unless the context requires a more limited range.

Phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

The transitional term "comprising," which is synonymous with "including," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, the singular forms "a," "an," and "the" include the plural reference unless the context clearly dictates otherwise.

In embodiments, a compound (e.g., an administered compound) is an isolated or purified compound. As used herein, an "isolated" or "purified" compound, is substantially free of cellular material or culture medium when produced by cells, or chemical precursors or other chemicals when chemically synthesized. In embodiments, purified compounds are at least 60% by weight (dry weight) the compound of interest. In embodiments, the preparation is at least 75%, more preferably at least 90%, and most preferably at least 99%, by weight the compound of interest. In embodiments, a purified compound is one that is at least 90%, 91%, 92%, 93%, 94%, 95%, 98%, 99%, or 100% (w/w) of the desired compound by weight. Purity may be measured by any appropriate standard method, for example, by column chromatography, thin layer chromatography, or high-performance liquid chromatography (HPLC) analysis. In embodiments, purified also defines a degree of sterility that is safe for administration to a human subject, e.g., lacking infectious or toxic agents.

A "combined synergistic amount" as used herein refers to the sum of a first amount (e.g., an amount of a pterostilbene) and a second amount (e.g., an amount of a megestrol acetate) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

"Pharmaceutically acceptable salts" is meant to include salts of the active compounds that are prepared with relatively nontoxic acids or bases, depending on the particular substituents found on the compounds described herein. In embodiments, when compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). In embodiments, a compound contains both basic and acidic functionalities that allow the compound to be converted into either base or acid addition salts.

Thus, the compounds disclosed herein may exist as salts, such as with pharmaceutically acceptable acids. Certain aspects include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by reducing cancer cell proliferation, reducing tumor growth or size, or reducing metastasis in a subject in need thereof. In embodiments, treatment achieves inhibition of disease (e.g., cancer) progression. As used herein, "inhibition" of disease progression or a disease complication in a subject means preventing or reducing the disease progression and/or a disease complication in the subject.

An "effective amount" is an amount sufficient to accomplish a stated purpose (e.g., achieve the effect for which it is administered, treat a disease, reduce cancer cell proliferation, reduce tumor growth or size, reduce metastasis, reduce one or more symptoms of a disease or condition, and the like). In embodiments, an effective amount of a single specified compound (e.g., a stilbenoid compound such as pterostilbene) is administered. In embodiments, an effective amount is the amount of two or more compounds in combination (e.g., a stilbenoid compound such as pterostilbene and a progestin such as megestrol acetate). In embodiments relating to an effective amount that is the amount of two or more compounds in combination, the amount of each compound would be an effective amount if the compound was administered singly, such that multiple effective amounts are combined. In embodiments relating to an effective amount that is the amount of two or more compounds in combination, the amount of one or more of the compounds is less than the effective amount of the compound(s) when administered alone, but the combination thereof is effective. An example of an "effective amount" is an amount sufficient to contribute to the treatment, prevention, or reduction of a symptom or symptoms of a disease (such as cancer, e.g., breast or endometrial cancer), which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, a "symptom" associated with a disorder includes any clinical or laboratory manifestation associated with the disorder, and is not limited to what the subject can feel or observe.

"Subject," "patient," and the like refer to a living organism who is a member of a species whose members may suffer from a disease or condition (e.g., cancer such as endometrial cancer or breast cancer) that can be treated by administration of a compound or pharmaceutical composition, as provided herein. Non-limiting examples include humans, other mammals such as primates, bovines, rats, mice, dogs, monkeys, goat, sheep, cows, deer, and other non-mammalian animals. In embodiments, a subject is human. In embodiments, a subject is male. In embodiments, a subject is female.

The terms "subject," "patient," "individual," and the like as used herein are not intended to be limiting and can be generally interchanged. That is, an individual described as a "patient" does not necessarily have a given disease, but may be merely seeking medical advice.

"Pharmaceutically acceptable excipient" and "pharmaceutically acceptable carrier" refer to a substance that aids the administration of an active agent to and absorption by a subject and can be included in the compositions provided herein without causing a significant adverse toxicological effect on the patient. Unless indicated to the contrary, the terms "active agent," "active ingredient," "therapeutically active agent," "therapeutic agent" and like are used synonymously. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, polyethylene glycol, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "administering" means oral administration, administration as an inhaled aerosol or as an inhaled dry powder, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "coadminister" it is meant that a composition or compound described herein is administered at the same time, just prior to, or just after the administration of one or more additional therapies, for example cancer therapies such as chemotherapy, hormonal therapy, radiotherapy, or immunotherapy. In embodiments, a composition or compound disclosed herein can be administered alone or can be coadministered to the patient. Coadministration is meant to include simultaneous or sequential administration of a compound or composition individually or in combination (more than one compound or agent). In embodiments, compositions provided herein can be delivered transdermally, by a topical route, formulated as applicator sticks, solutions, suspensions, emulsions, gels, creams, ointments, nanoparticles, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. In embodiments, compositions provided herein may additionally include components to provide sustained release and/or comfort. Such components include high molecular weight, anionic mucomimetic polymers, gelling polysaccharides and finely-divided drug carrier substrates. Non-limiting examples of these components are discussed in greater detail in U.S. Pat. Nos. 4,911,920; 5,403,841; 5,212,162; and 4,861,760. The entire contents of these patents are incorporated herein by reference in their entirety for all purposes. In embodiments, compositions provided herein can also be delivered as microspheres for slow release in the body. For example, microspheres can be administered via intradermal injection of drug-containing microspheres, which slowly release subcutaneously (see Rao, *J Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, compositions provided herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions provided herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Pharmaceutical compositions provided by herein include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition (e.g. cancer or cancer subtype) being treated. Determination of a therapeutically effective amount of a compound of the invention is well within the capabilities of those skilled in the art, especially in light of the detailed disclosure herein.

The dosage and frequency (single or multiple doses) administered to a subject can vary depending upon a variety of factors, for example, whether the subject suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions provided herein. Adjustment and manipulation of established dosages (e.g., frequency and duration) are well within the ability of those skilled in the art.

As used herein, the term "progestin" refers to natural or synthetic steroidal hormones that cause progestational activity. Non-limiting examples of progestins include progesterone, megestrol, megestrol acetate, levonorgestrel, medroxyprogesterone (e.g., Depo-Provera™), medoxyprogesterone acetate, norethindrone, and norethindrone acetate. In embodiments, the progesterone is micronized progesterone.

As used herein, the term "stilbenoid compound" refers to a hydroxylated derivative of stilbene, which belongs to the family of phenylpropanoids. Non-limiting examples of stilbenoid compounds include resveratrol, isorhapontigenin, piceatannol, oxyresveratrol, rhapontigenin, gnetol, and pterostilbene.

The chemical structure of pterostilbene is as follows:

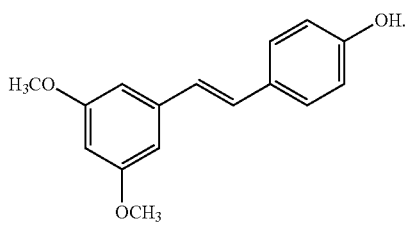 [SMILES: COc1cc(/C=C/c2ccc(O)cc2)cc(OC)c1]

The PubChem CID for pterostilbene is 5281727.

The chemical structure of resveratrol is as follows:

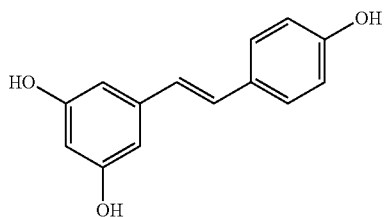 [SMILES: Oc1ccc(/C=C/c2cc(O)cc(O)c2)cc1]

The PubChem CID for resveratrol is 445154.

The chemical structure of isorhapontigenin is as follows:

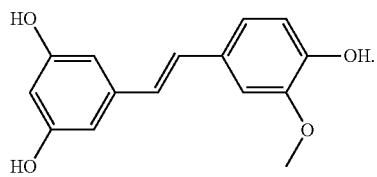 [SMILES: COc1cc(/C=C/c2cc(O)cc(O)c2)ccc1O]

The PubChem CID for isorhapontigenin is 5318650.

The chemical structure of piceatannol is as follows:

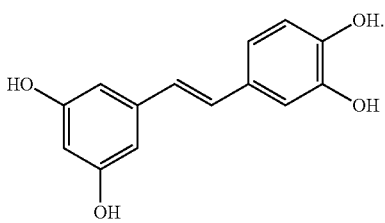 [SMILES: Oc1cc(O)cc(/C=C/c2ccc(O)c(O)c2)c1]

The PubChem CID for piceatannol is 667639.

The chemical structure of oxyresveratrol is as follows:

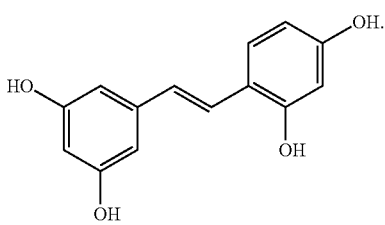 [SMILES: Oc1cc(O)cc(/C=C/c2ccc(O)cc2O)c1]

The PubChem CID for oxyresveratrol is 5281717.

The chemical structure of rhapontigenin is as follows:

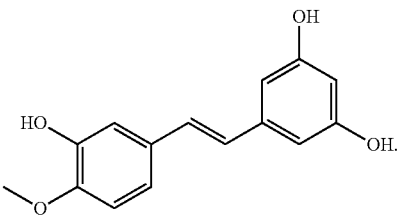 [SMILES: COc1ccc(/C=C/c2cc(O)cc(O)c2)cc1O]

The PubChem CID for rhapontigenin is 5320954.

The chemical structure of gnetol is as follows:

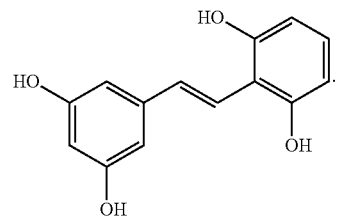 [SMILES: Oc1cc(O)cc(/C=C/c2c(O)cccc2O)c1]

The PubChem CID for gnetol is 45382232.

The chemical structure of megestrol is as follows:

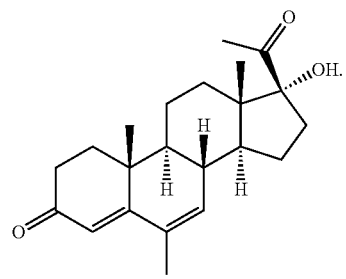

The PubChem CID for megestrol is 19090.

The chemical structure of megestrol acetate is as follows:

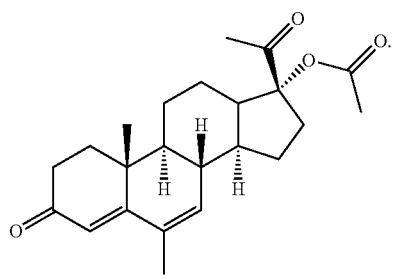

The PubChem CID for megestrol acetate is 11683.

The chemical structure of medroxyprogesterone is as follows:

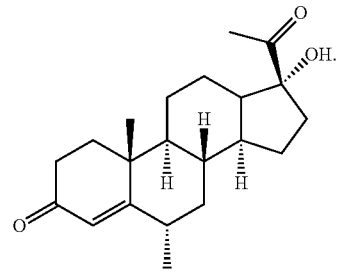

The PubChem CID for medroxyprogesterone is 10631.

The chemical structure of progesterone is as follows:

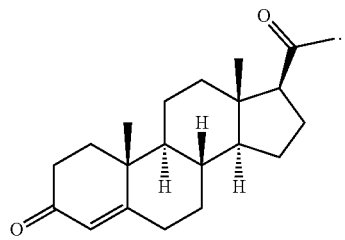

The PubChem CID for progesterone is 5994.

The chemical structure of norethisterone acetate is as follows:

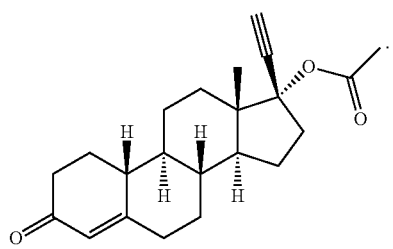

The ChemSpider ID for norethisterone acetate is 63021.

The chemical structure of levonorgestrel is as follows:

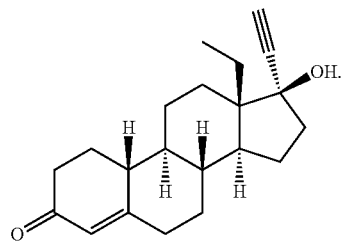

The PubChem CID for levonorgestrel is 13109.

ARID1A is also known as AT-rich interaction domain 1A, and includes any recombinant or naturally-occurring form of AT-rich interaction domain-containing protein 1A, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring AT-rich interaction domain-containing protein 1A. In embodiments, the ARID1A gene is substantially identical to the nucleic acid identified by the ENSEMBLE reference number ENSG00000117713 or a variant having substantial identity thereto. A non-limiting example of an amino acid sequence for an ARID1A protein is provided in NCBI Accession No. NP_006006.3. A non-limiting example of a nucleotide sequence that encodes ARID1A is provided in NCBI Accession No. NM_006015.5.

CTNNB1 is also known as catenin beta 1, and includes any recombinant or naturally-occurring form of catenin beta-1, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring catenin beta-1 protein. In embodiments, the CTNNB1 gene is substantially identical to the nucleic acid identified by the ENSEMBLE reference number ENSG00000168036 or a variant having substantial identity thereto. A non-limiting example of an amino acid sequence for a CTNNB1 protein is provided in NCBI Accession No. NP_001091679.1. A non-limiting example of a nucleotide sequence that encodes CTNNB1 is provided in NCBI Accession No. NM_001098209.1.

FGFR2 is also known as fibroblast growth factor 2, and includes any recombinant or naturally-occurring form of fibroblast growth factor 2, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring fibroblast growth factor 2 protein. In embodiments, the FGFR2 gene is substantially identical to the nucleic acid identified by the ENSEMBLE reference number ENSG00000066468 or a variant having substantial identity thereto. A non-limiting example of an amino acid sequence for a FGFR2 protein is provided in NCBI Accession No. NP_000132.3. A non-limiting example of a nucleotide sequence that encodes FGFR2 is provided in NCBI Accession No. NM_000141.4.

KRAS includes any recombinant or naturally-occurring form of KRAS, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring KRAS protein. In embodiments, the KRAS gene is substantially identical to the nucleic acid identified by the ENSEMBLE reference number ENSG00000133703 or a variant having substantial identity thereto. A non-limiting example of an amino acid sequence for a KRAS protein is provided in NCBI Accession No. NP_203524.1. A non-limiting example of a nucleotide sequence that encodes CTNNB1 is provided in NCBI Accession No. NM_033360.3.

PIK3R1 is also known as phosphatidylinositol 3-kinase regulatory subunit alpha, and includes any recombinant or naturally-occurring form of phosphatidylinositol 3-kinase regulatory subunit alpha, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring phosphatidylinositol 3-kinase regulatory subunit alpha protein. In embodiments, the PIK3R1 gene is substantially identical to the nucleic acid identified by the ENSEMBLE reference number ENSG00000145675 or a variant having substantial identity thereto. A non-limiting example of an amino acid sequence for a PIK3R1 protein is provided in NCBI Accession No. NP_852664.1. A non-limiting example of a nucleotide sequence that encodes PIK3R1 is provided in NCBI Accession No. NM_181523.2.

TP53 is also known as tumor protein p53, and includes any recombinant or naturally-occurring form of tumor protein p53, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring tumor protein p53. In embodiments, the TP53 gene is substantially identical to the nucleic acid identified by the ENSEMBLE reference number ENSG00000141510 or a variant having substantial identity thereto. A non-limiting example of an amino acid sequence for a TP53 protein is provided in NCBI Accession No. NP_000537.3. A non-limiting example of a nucleotide sequence that encodes TP53 is provided in NCBI Accession No. NM_000546.5.

PTEN is also known as phosphatase and tensin homolog, and includes any recombinant or naturally-occurring form of phosphatase and tensin homolog, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring phosphatase and tensin homolog protein. In embodiments, the PTEN gene is substantially identical to the nucleic acid identified by the ENSEMBLE reference number ENSG00000171862 or a variant having substantial identity thereto. A non-limiting example of an amino acid sequence for a PTEN protein is provided in NCBI Accession No. NP_000305.3. A non-limiting example of a nucleotide sequence that encodes PTEN is provided in NCBI Accession No. NM_000314.6.

PPP2R1A is also known as serine/threonine-protein phosphatase 2A 65 kDa regulatory subunit A alpha isoform, and includes any recombinant or naturally-occurring form of serine/threonine-protein phosphatase 2A 65 kDa regulatory subunit A alpha isoform, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring serine/threonine-protein phosphatase 2A 65 kDa regulatory subunit A alpha isoform. In embodiments, the PPP2R1A gene is substantially identical to the nucleic acid identified by the ENSEMBLE reference number ENSG00000105568 or a variant having substantial identity thereto. A non-limiting example of an amino acid sequence for a PPP2R1A protein is provided in NCBI Accession No. NP_055040.2. A non-limiting example of a nucleotide sequence that encodes PPP2R1A is provided in NCBI Accession No. NM_014225.5.

PIK3CA is also known as phosphatidylinositol-4,5-bisphosphate 3-kinase catalytic subunit alpha, and includes any recombinant or naturally-occurring form of phosphatidylinositol-4,5-bisphosphate 3-kinase catalytic subunit alpha, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring phosphatidylinositol-4,5-bisphosphate 3-kinase catalytic subunit alpha. In embodiments, the PIK3CA gene is substantially identical to the nucleic acid identified by the ENSEMBLE reference number ENSG00000121879 or a variant having substantial identity thereto. A non-limiting example of an amino acid sequence for a PIK3CA protein is provided in NCBI Accession No. NP_006209.2. A non-limiting example of a nucleotide sequence that encodes PIK3CA is provided in NCBI Accession No. NM_006218.3.

PIK3R1 is also known as phosphatidylinositol 3-kinase regulatory subunit alpha enzyme, and includes any recombinant or naturally-occurring form of phosphatidylinositol 3-kinase regulatory subunit alpha enzyme, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring phosphatidylinositol 3-kinase regulatory subunit alpha enzyme. In embodiments, the PIK3R1 gene is substantially identical to the nucleic acid identified by the ENSEMBLE reference number ENSG00000145675 or a variant having substantial identity thereto. A non-limiting example of an amino acid sequence for a PIK3R1 protein is provided in NCBI Accession No. NP_852664.1. A non-limiting example of a nucleotide sequence that encodes PIK3R1 is provided in NCBI Accession No. NM_181523.2.

STK15 is also known as serine/threonine-protein kinase 6, and includes any recombinant or naturally-occurring form of serine/threonine-protein kinase 6, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring serine/threonine-protein kinase 6. In embodiments, the STK15 gene is substantially identical to the nucleic acid identified by the ENSEMBLE reference number ENSG00000087586 or a variant having substantial identity thereto. A non-limiting example of an amino acid sequence for a STK15 protein is provided in NCBI Accession No. NP_001310232.1. A non-limiting example of a nucleotide sequence that encodes STK15 is provided in NCBI Accession No. NM_001323303.1.

CCNE1 is also known as G1/S-specific cyclin-E1, and includes any recombinant or naturally-occurring form of G1/S-specific cyclin-E1, and homologs, isoform, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring G1/S-specific cyclin-E1 protein. In embodiments, the CCNE1 gene is substantially identical to the nucleic acid identified by the ENSEMBLE reference number ENSG00000105173 or a variant having substantial identity thereto. A non-limiting example of an amino acid sequence for a CCNE1 protein is provided in NCBI Accession No. NP_001229.1. A non-limiting example of a nucleotide sequence that encodes CCNE1 is provided in NCBI Accession No. NM_001238.3.

ERBB2 is also known as receptor tyrosine-protein kinase erbB-2, and includes any recombinant or naturally-occurring form of receptor tyrosine-protein kinase erbB-2, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring receptor tyrosine-protein kinase erbB-2. In embodiments, the ERBB2 gene is substantially identical to the nucleic acid identified by the ENSEMBLE reference number ENSG00000141736 or a variant having substantial identity thereto. A non-limiting example of an amino acid sequence for a ERBB2 protein is provided in NCBI Accession No. NP_004439.2. A non-limiting example of a nucleotide sequence that encodes ERBB2 is provided in NCBI Accession No. NM_004448.3.

CCND1 is also known as cyclin-D1, and includes any recombinant or naturally-occurring form of cyclin-D1, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring cyclin-D1 protein. In embodiments, the CCND1 gene is substantially identical to the nucleic acid identified by the ENSEMBLE reference number ENSG00000110092 or a variant having substantial identity thereto. A non-limiting example of an amino acid sequence for a CCND1 protein is provided in NCBI Accession No. NP_444284.1. A non-limiting example of a nucleotide sequence that encodes CCND1 is provided in NCBI Accession No. NM_053056.2.

MLH1 is also known as DNA mismatch repair protein Mlh1, and includes any recombinant or naturally-occurring form of DNA mismatch repair protein Mlh1, and homologs, isoforms, or variants thereof. In embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DNA mismatch repair protein Mlh1. In embodiments, the MLH1 gene is substantially identical to the nucleic acid identified by the ENSEMBLE reference number ENSG00000076242 or a variant having substantial identity thereto. A non-limiting example of an amino acid sequence for a MLH1 protein is provided in NCBI Accession No. NP_000240.1. A non-limiting example of a nucleotide sequence that encodes MLH1 is provided in NCBI Accession No. NM_000249.3.

RASSF1A is also known as Ras association domain-containing protein 1, and includes any recombinant or naturally-occurring form of Ras association domain-containing protein 1, homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Ras association domain-containing protein 1. In embodiments, the RASSF1A gene is substantially identical to the nucleic acid identified by the ENSEMBLE reference number ENSG00000068028 or a variant having substantial identity thereto. A non-limiting example of an amino acid sequence for a RASSF1A protein is provided in NCBI Accession No. NP_009113.3. A non-limiting example of a nucleotide sequence that encodes RASSF1A is provided in NCBI Accession No. NM_007182.4.

SPRY2 is also known as protein sprouty homolog 2, and includes any of the recombinant or naturally-occurring form of sprouty homolog 2, and homologs, isoforms, or variants thereof. In embodiments, homolgos, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring protein sprouty homolog 2. In embodiments, the SPRY2 gene is substantially identical to the nucleic acid identified by the ENSEMBLE reference number ENSG00000136158 or a variant having substantial identity thereto. A non-limiting example of an amino acid sequence for a SPRY2 protein is provided in NCBI Accession No. NP_001305465.1. A non-limiting example of a nucleotide sequence that encodes SPRY2 is provided in NCBI Accession No. NM_001318536.1.

CDKN2A is also known as cyclin-dependent kinase inhibitor 2A, and includes any recombinant or naturally-occurring form of cyclin-dependent kinase inhibitor 2A, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring cyclin-dependent kinase inhibitor 2A and/or tumor suppressor ARF protein. In embodiments, the CDKN2A gene is substantially identical to the nucleic acid identified by the ENSEMBLE reference number ENSG00000147889 or a variant having substantial identity thereto. A non-limiting example of an amino acid sequence for a CDKN2A protein is provided in NCBI Accession No. NP_000068.1. A non-limiting example of a nucleotide sequence that encodes CDKN2A is provided in NCBI Accession No. NM_000077.4.

Estrogen receptors (ERs) are a group of proteins found inside and on cells. They are receptors that are activated by the hormone estrogen (17β-estradiol). Two classes of ER exist: nuclear estrogen receptors (ERα and ERβ), which are members of the nuclear receptor family of intracellular receptors, and membrane estrogen receptors (mERs) (GPER (GPR30), ER-X, and $G_q$-mER), which are mostly G protein-coupled receptors.

Estrogen receptor alpha is also known as NR3A1, and includes any recombinant or naturally-occurring form of estrogen receptor alpha, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring estrogen receptor alpha. In embodiments, the estrogen receptor alpha gene is substantially identical to the nucleic acid identified by the ENSEMBLE reference number ENSG00000091831 or a variant having substantial identity thereto. A non-limiting example of an amino acid sequence for an estrogen receptor alpha protein is provided in NCBI Accession No. NP_000116.2. A non-limiting example of a nucleotide sequence that encodes estrogen receptor alpha is provided in NCBI Accession No. NM_000125.3.

Estrogen receptor beta is also known as NR3A2, and includes any recombinant or naturally-occurring form of estrogen receptor beta, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring estrogen receptor beta. In embodiments, the estrogen receptor beta gene is substantially identical to the nucleic acid identified by the ENSEMBLE reference number ENSG00000140009 or a variant having substantial identity thereto. A non-limiting example of an amino acid sequence for an estrogen receptor beta protein is provided in NCBI Accession No. NP_001035365.1. A non-limiting example of a nucleotide sequence that encodes estrogen receptor beta is provided in NCBI Accession No. NM_001040275.1.

Progesterone receptor is also known as NR3C3, and includes any recombinant or naturally-occurring form of progesterone receptor, and homologs, isoforms, or variants thereof. In embodiments, homologs, isoforms, or variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring progesterone receptor. In embodiments, the progesterone receptor gene is substantially identical to the nucleic acid identified by the ENSEMBLE reference number ENSG00000082175 or a variant having substantial identity thereto. Non-limiting examples of amino acid sequences for progesterone receptor proteins are provided in NCBI Accession Nos. NP_001189403.1, NP_000917.3, NP_001258090.1, and NP_001258091.1. Non-limiting examples of nucleotide sequences that encode progesterone receptors are provided in NCBI Accession Nos. NM_001202474.3, NM_000926.4, NM_001271161.2, and NM_001271162.1. In embodiments, the progesterone receptor is progesterone receptor isoform A. A non-limiting example of an amino acid sequence for progesterone receptor isoform A is provided in NCBI Accession No. NP_001189403.1. A non-limiting example of a nucleotide sequence that encodes progesterone receptor isoform A is provided in NCBI Accession No. NM_001202474.3. In embodiments, the progesterone receptor is progesterone receptor isoform B. A non-limiting example of an amino acid sequence for progesterone receptor isoform B is provided in NCBI Accession No. NP_000917.3. A non-limiting example of a nucleotide sequence that encodes progesterone receptor isoform B is provided in NCBI Accession No. NM_000926.4. In embodiments, the progesterone receptor is progesterone receptor isoform C. A non-limiting example of an amino acid sequence for progesterone receptor isoform C is provided in NCBI Accession No. NP_001258090.1. A non-limiting example of a nucleotide sequence that encodes progesterone receptor isoform C is provided in NCBI Accession No. NM_001271161.2.

Percentage of sequence identity may be determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In embodiments, two sequences are 100% identical. In embodiments, two sequences are 100% identical over the entire length of one of the sequences (e.g., the shorter of the two sequences where the sequences have different lengths). In embodiments, identity may refer to the complement of a test sequence. In some embodiments, the identity exists over a region that is at least about 10 to about 100, about 20 to about 75, about 30 to about 50 amino acids or nucleotides in length. In embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In embodiments, a comparison window is the entire length of one or both of two aligned sequences. In embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In embodiments, algorithms that are suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information (NCBI), as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

Lynch syndrome, often called hereditary nonpolyposis colorectal cancer (HNPCC), is an inherited disorder that increases the risk of many types of cancer, particularly cancers of the colon (large intestine) and rectum, which are collectively referred to as colorectal cancer. People with Lynch syndrome also have an increased risk of cancers of the stomach, small intestine, liver, gallbladder ducts, upper urinary tract, brain, and skin. Additionally, women with this disorder have a high risk of cancer of the ovaries and lining of the uterus (the endometrium). People with Lynch syndrome may occasionally have noncancerous (benign) growths (polyps) in the colon, called colon polyps. In individuals with this disorder, colon polyps occur earlier but not in greater numbers than they do in the general population. Additional non-limiting features of Cowden syndrome are described in the U.S. National Library of Medicine's Genetics Home Reference entry for "Lynch syndrome", which is available at ghr.nlm.nih.gov/condition/lynch-syndrome.

Cowden syndrome is an autosomal-dominant syndrome with a PTEN germline mutation, predisposing patients to a lifetime risk of 5-10% for endometrial cancer. Cowden syndrome is a disorder characterized by multiple noncancerous, tumor-like growths called hamartomas and an increased risk of developing certain cancers. Almost everyone with Cowden syndrome develops hamartomas. These growths are most commonly found on the skin and mucous membranes (such as the lining of the mouth and nose), but they can also occur in the intestine and other parts of the body. The growth of hamartomas on the skin and mucous membranes typically becomes apparent by a person's late twenties. Cowden syndrome is associated with an increased risk of developing several types of cancer, particularly cancers of the breast, a gland in the lower neck called the thyroid, and the lining of the uterus (the endometrium). Other cancers that have been identified in people with Cowden syndrome include colorectal cancer, kidney cancer, and a form of skin cancer called melanoma. Compared with the general population, people with Cowden syndrome develop these cancers at younger ages, often beginning in their thirties or forties. Other diseases of the breast, thyroid, and endometrium are also common in Cowden syndrome. Additional signs and symptoms can include an enlarged head (macrocephaly) and a rare, noncancerous brain tumor called Lhermitte-Duclos disease. A small percentage of affected individuals have delayed development or intellectual disability. Additional non-limiting features of Cowden syndrome are described in the U.S. National Library of Medicine's Genetics Home Reference entry for "Cowden syndrome", which is available at ghr.nlm.nih.gov/condition/cowden-syndrome.

Methods of Treatment

In an aspect, included herein a method of treating cancer in a subject in need thereof, the method including administering to the subject a therapeutically effective amount of (i) a stilbenoid compound; and (ii) a progestin. In embodiments, a combination comprising a therapeutically effective amount of (i) a stilbenoid compound (e.g., resveratrol, isorhapontigenin, piceatannol, oxyresveratrol, rhapontigenin, gnetol, or pterostilbene); and (ii) a progestin (e.g., progesterone, megestrol, megestrol acetate, levonorgestrel, medroxyprogesterone, medoxyprogesterone acetate, norethindrone, and norethindrone acetate) is administered to the subject. In embodiments, a combination consisting essentially of (i) a stilbenoid compound (e.g., resveratrol, isorhapontigenin, piceatannol, oxyresveratrol, rhapontigenin, gnetol, or pterostilbene); and (ii) a progestin (e.g., progesterone, megestrol, megestrol acetate, levonorgestrel, medroxyprogesterone, medoxyprogesterone acetate, norethindrone, and norethindrone acetate) is administered to the subject. In embodiments, a combination consisting of (i) a stilbenoid compound (e.g., resveratrol, isorhapontigenin, piceatannol, oxyresveratrol, rhapontigenin, gnetol, or pterostilbene); and (ii) a progestin (e.g., progesterone, megestrol, megestrol acetate, levonorgestrel, medroxyprogesterone, medoxyprogesterone acetate, norethindrone, and norethindrone acetate) is administered to the subject. In embodiments, no other active agent that is used to kill or inhibit the proliferation of cancer cells is administered to the subject.

In embodiments, the stilbenoid compound is resveratrol, isorhapontigenin, piceatannol, oxyresveratrol, rhapontigenin, gnetol, pterostilbene, or a pharmaceutically acceptable salt thereof. In embodiments, the stilbenoid is resveratrol or a pharmaceutically acceptable salt thereof. In embodiments, the stilbenoid is isorhapontigenin or a pharmaceutically acceptable salt thereof. In embodiments, the stilbenoid is piceatannol or a pharmaceutically acceptable salt thereof. In embodiments, the stilbenoid is oxyresveratrol or a pharmaceutically acceptable salt thereof. In embodiments, the stilbenoid is rhapontigenin or a pharmaceutically acceptable salt thereof. In embodiments, the stilbenoid is gnetol or a pharmaceutically acceptable salt thereof. In embodiments, the stilbenoid is pterostilbene or a pharmaceutically acceptable salt thereof.

In embodiments, the progestin is progesterone. In embodiments, the progestin is medroxyprogesterone or a pharmaceutically acceptable salt thereof (e.g., medoxyprogesterone acetate or "MPA"), norethindrone or a pharmaceutically acceptable salt thereof (e.g., norethindrone acetate), micronized progesterone, depot MPA, levonorgestrel, or megestrol. In embodiments, the progestin is medroxyprogesterone or a pharmaceutically acceptable salt thereof (e.g., medoxyprogesterone acetate). In embodiments, the progestin is micronized progesterone. In embodiments, the progestin is depot MPA. In embodiments, the progestin is norethindrone acetate. In embodiments, the progestin is levonorgestrel. In embodiments, the levonorgestrel is in a levonorgestrel-releasing intrauterine device (e.g., LNg20 or Mirena®). In embodiments, the progestin is megestrol or a pharmaceutically acceptable salt thereof (e.g., megestrol acetate). In embodiments, a progestin binds to a nuclear progesterone receptor (nPR).

In an aspect, provided herein is a method of treating cancer in a subject in need thereof, the method including administering to the subject a therapeutically effective amount of (i) pterostilbene or a pharmaceutically acceptable salt thereof; and (ii) megestrol or a pharmaceutically acceptable salt thereof.

In an aspect, provided herein is a method of preventing or reducing the risk of cancer in a subject who does not have the cancer, the method including administering to the subject a therapeutically effective amount of (i) pterostilbene or a pharmaceutically acceptable salt thereof; and (ii) megestrol or a pharmaceutically acceptable salt thereof.

In an aspect, provided herein is a method of preventing cancer in a subject who is at risk of cancer, the method including administering to the subject a therapeutically effective amount of (i) pterostilbene or a pharmaceutically acceptable salt thereof; and (ii) megestrol or a pharmaceutically acceptable salt thereof.

In an aspect, provided herein is a method of reducing the likelihood that a subject will develop cancer, the method including administering to the subject a therapeutically effective amount of (i) pterostilbene or a pharmaceutically acceptable salt thereof; and (ii) megestrol or a pharmaceutically acceptable salt thereof.

In embodiments, the therapeutically effective amount is a combined synergistic amount.

In embodiments, pterostilbene is administered to the subject.

In an aspect, provided herein is a method of treating ER positive and/or PR positive cancer in a subject in need thereof, including administering a therapeutically effective amount of pterostilbene or a pharmaceutically acceptable salt thereof to the subject. In embodiments, ER positive cancer includes cancer cells that express ER (e.g., ER-α or ER-β). In embodiments, ER positive cancer includes cancer cells that express more ER (e.g., ER-α or ER-β) compared to normal cells or tissue of the same type. In embodiments, the ER is expressed on the plasma membranes of cancer cells. In embodiments, the ER is a nuclear ER. In embodiments, PR positive cancer includes cancer cells that express PR. In embodiments, PR positive cancer includes cancer cells that express more PR compared to normal cells or tissue of the same type. In embodiments, the PR is expressed on the plasma membranes of cancer cells. In embodiments, the PR is a nuclear PR. In embodiments, the PR is a cytoplasmic PR. In embodiments, the PR is nuclear and cytoplasmic PR. In embodiments, the PR is isoform A of PR. In embodiments, the PR is isoform B of PR. In embodiments, the PR is isoform C of PR. Methods for identifying ER and PR positive endometrial cancer are well known in the art. Non-limiting descriptions relating to ER and PR positive endometrial cancer are provided in Singh et al. (2007) Gynecol Oncol. 106(2):325, the entire contents of which are incorporated herein by reference.

In embodiments, the pterostilbene is administered at a dose of less than 280 mg. In embodiments, the pterostilbene is administered at a dose of less than 270 mg. In embodiments, the pterostilbene is administered at a dose of less than 260 mg. In embodiments, the pterostilbene is administered at a dose of less than 250 mg. In embodiments, the pterostilbene is administered at a dose of less than 240 mg. In embodiments, the pterostilbene is administered at a dose of less than 230 mg. In embodiments, the pterostilbene is administered at a dose of less than 220 mg. In embodiments, the pterostilbene is administered at a dose of less than 210 mg. In embodiments, the pterostilbene is administered at a dose of less than 200 mg. In embodiments, the pterostilbene is administered at a dose of less than 190 mg. In embodiments, the pterostilbene is administered at a dose of less than 180 mg. In embodiments, the pterostilbene is administered at a dose of less than 170 mg. In embodiments, the pterostilbene is administered at a dose of less than 160 mg. In embodiments, the pterostilbene is administered at a dose of less than 150 mg. In embodiments, the pterostilbene is administered at a dose of less than 140 mg. In embodiments, the pterostilbene is administered at a dose of less than 130 mg. In embodiments, the pterostilbene is administered at a dose of less than 120 mg. In embodiments, the pterostilbene is administered at a dose of less than 110 mg. In embodiments, the pterostilbene is administered at a dose of less than 100 mg. In embodiments, the pterostilbene is administered at a dose of less than 90 mg. In embodiments, the pterostilbene is administered at a dose of less than 80 mg. In embodiments, the pterostilbene is administered at a dose of less than 75 mg. In embodiments, the pterostilbene is administered at a dose of less than 70 mg. In embodiments, the pterostilbene is administered at a dose of less than 65 mg. In embodiments, the pterostilbene is administered at a dose of less than 60 mg. In embodiments, the pterostilbene is administered at a dose of less than 55 mg. In embodiments, the pterostilbene is administered at a dose of less than 50 mg. In embodiments, the pterostilbene is administered at a dose of less than 48 mg. In embodiments, the pterostilbene is administered at a dose of less than 46 mg. In embodiments, the pterostilbene is administered at a dose of less than 44 mg. In embodiments, the pterostilbene is administered at a dose of less than 42 mg. In embodiments, the pterostilbene is administered at a dose of less than 40 mg. In embodiments, the pterostilbene is administered at a dose of less than 38 mg. In embodiments, the pterostilbene is administered at a dose of less than 36 mg. In embodiments, the pterostilbene is administered at a dose of less than 34 mg. In embodiments, the pterostilbene is administered at a dose of less than 32 mg. In embodiments, the pterostilbene is administered at a dose of less than 30 mg. In embodiments, the pterostilbene is administered at a dose of less than 28 mg. In embodiments, the pterostilbene is administered at a dose of less than 26 mg. In embodiments, the pterostilbene is administered at a dose of less than 24 mg. In embodiments, the pterostilbene is administered at a dose of less than 22 mg. In embodiments, the pterostilbene is administered at a dose of less than 20 mg. In embodiments, the pterostilbene is administered at a dose of at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg, but less than an amount indicated above. In embodiments, the pterostilbene is administered at a dose of at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg. In embodiments, the pterostilbene is administered at a dose of at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg, but less than 300 mg, 250 mg, 200 mg, 150 mg, or 100 mg.

In embodiments, the pterostilbene is administered (e.g., at a dose disclosed herein or another dose) at least 1, 2, 3, 4, or 5 times per day, per week, or per month. In embodiments, the pterostilbene is administered (e.g., at a dose disclosed herein or another dose) 1, 2, 3, 4, or 5 times per day, per week, or per month. In embodiments, the pterostilbene is administered (e.g., at a dose disclosed herein or another dose) about 1, 2, 3, 4, or 5 times per day, per week, or per month. In embodiments, the pterostilbene is administered once per day. In embodiments, the pterostilbene is administered twice per day.

In embodiments, the pterostilbene is administered orally.

In embodiments, the megestrol or the pharmaceutically acceptable salt thereof is megestrol acetate.

In embodiments, the megestrol acetate is administered at a dose of 40 mg to 800 mg. In embodiments, the megestrol acetate is administered at a dose of 40 mg to 750 mg. In embodiments, the megestrol acetate is administered at a dose of 40 mg to 700 mg. In embodiments, the megestrol acetate is administered at a dose of 40 mg to 650 mg. In embodiments, the megestrol acetate is administered at a dose of 40 mg to 600 mg. In embodiments, the megestrol acetate is administered at a dose of 40 mg to 550 mg. In embodiments, the megestrol acetate is administered at a dose of 40 mg to 500 mg. In embodiments, the megestrol acetate is administered at a dose of 40 mg to 450 mg. In embodiments, the megestrol acetate is administered at a dose of 40 mg to 400 mg. In embodiments, the megestrol acetate is administered at a dose of 40 mg to 350 mg. In embodiments, the megestrol acetate is administered at a dose of 40 mg to 320 mg. In embodiments, the megestrol acetate is administered at a dose of 45 mg to 320 mg. In embodiments, the megestrol acetate is administered at a dose of 50 mg to 320 mg. In embodiments, the megestrol acetate is administered at a dose of 60 mg to 320 mg. In embodiments, the megestrol acetate is administered at a dose of 70 mg to 320 mg. In embodiments, the megestrol acetate is administered at a dose of 80 mg to 320 mg. In embodiments, the megestrol acetate is administered at a dose of 90 mg to 320 mg. In embodiments, the megestrol acetate is administered at a dose of 100 mg to 320 mg. In embodiments, the megestrol acetate is administered at a dose of 110 mg to 320 mg. In embodiments, the megestrol acetate is administered at a dose of 120 mg to 320 mg. In embodiments, the megestrol acetate is administered at a dose of 130 mg to 320 mg. In embodiments, the megestrol acetate is administered at a dose of 140 mg to 320 mg. In embodiments, the megestrol acetate is administered at a dose of 150 mg to 320 mg. In embodiments, the megestrol acetate is administered at a dose of 160 mg to 320 mg. In embodiments, the megestrol acetate is administered at a dose of 170 mg to 320 mg. In embodiments, the megestrol acetate is administered at a dose of 180 mg to 320 mg. In embodiments, the megestrol acetate is administered at a dose of 190 mg to 320 mg. In embodiments, the megestrol acetate is administered at a dose of 200 mg to 320 mg. In embodiments, the megestrol acetate is administered at a dose of 210 mg to 320 mg. In embodiments, the megestrol acetate is administered at a dose of 220 mg to 320 mg. In embodiments, the megestrol acetate is administered at a dose of 230 mg to 320 mg. In embodiments, the megestrol acetate is administered at a dose of 240 mg to 320 mg. In embodiments, the megestrol acetate is administered at a dose of 250 mg to 320 mg. In embodiments, the megestrol acetate is administered at a dose of 260 mg to 320 mg. In embodiments, the megestrol acetate is administered at a dose of 270 mg to 320 mg. In embodiments, the megestrol acetate is administered at a dose of 280 mg to 320 mg. In embodiments, the megestrol acetate is administered at a dose of 290 mg to 320 mg. In embodiments, the megestrol acetate is administered at a dose of 300 mg to 320 mg. In embodiments, the megestrol acetate is administered at a dose of 310 mg to 320 mg. In embodiments, the megestrol acetate is administered at a dose of 310 mg to 315 mg.

In embodiments, the megestrol acetate is administered at a dose of 40 mg to 310 mg. In embodiments, the megestrol acetate is administered at a dose of 40 mg to 300 mg. In embodiments, the megestrol acetate is administered at a dose of 40 mg to 290 mg. In embodiments, the megestrol acetate is administered at a dose of 40 mg to 280 mg. In embodiments, the megestrol acetate is administered at a dose of 40 mg to 270 mg. In embodiments, the megestrol acetate is administered at a dose of 40 mg to 260 mg. In embodiments, the megestrol acetate is administered at a dose of 40 mg to 250 mg. In embodiments, the megestrol acetate is administered at a dose of 40 mg to 240 mg. In embodiments, the megestrol acetate is administered at a dose of 40 mg to 230 mg. In embodiments, the megestrol acetate is administered at a dose of 40 mg to 220 mg. In embodiments, the megestrol acetate is administered at a dose of 40 mg to 200 mg. In embodiments, the megestrol acetate is administered at a dose of 40 mg to 190 mg. In embodiments, the megestrol acetate is administered at a dose of 40 mg to 180 mg. In embodiments, the megestrol acetate is administered at a dose of 40 mg to 170 mg. In embodiments, the megestrol acetate is administered at a dose of 40 mg to 160 mg. In embodiments, the megestrol acetate is administered at a dose of 40 mg to 150 mg. In embodiments, the megestrol acetate is administered at a dose of 40 mg to 140 mg. In embodiments, the megestrol acetate is administered at a dose of 40 mg to 130 mg. In embodiments, the megestrol acetate is administered at a dose of 40 mg to 120 mg. In embodiments, the megestrol acetate is administered at a dose of 40 mg to 110 mg. In embodiments, the megestrol acetate is administered at a dose of 40 mg to 100 mg. In embodiments, the megestrol acetate is administered at a dose of 40 mg to 90 mg. In embodiments, the megestrol acetate is administered at a dose of 40 mg to 80 mg. In embodiments, the megestrol acetate is administered at a dose of 40 mg to 70 mg. In embodiments, the megestrol acetate is administered at a dose of 40 mg to 60 mg. In embodiments, the megestrol acetate is administered at a dose of 40 mg to 50 mg. In embodiments, the megestrol acetate is administered at a dose of 40 mg to 45 mg.

In embodiments, the megestrol acetate is administered at a dose of less than 800 mg. In embodiments, the megestrol acetate is administered at a dose of less than 700 mg. In embodiments, the megestrol acetate is administered at a dose of less than 600 mg. In embodiments, the megestrol acetate is administered at a dose of less than 500 mg. In embodiments, the megestrol acetate is administered at a dose of less than 400 mg. In embodiments, the megestrol acetate is administered at a dose of less than 300 mg. In embodiments, the megestrol acetate is administered at a dose of less than 200 mg. In embodiments, the megestrol acetate is administered at a dose of less than 100 mg. In embodiments, the megestrol acetate is administered at a dose of less than 50 mg. In embodiments, the megestrol acetate is administered at a dose of less than 40 mg. In embodiments, the megestrol acetate is administered at a dose of less than 30 mg. In embodiments, the megestrol acetate is administered at a dose of less than 20 mg. In embodiments, the megestrol acetate is administered at a dose of less than 15 mg. In embodiments, the megestrol acetate is administered at a dose of less than 10 mg. In embodiments, the megestrol acetate is administered at a dose of less than 9 mg. In embodiments, the megestrol acetate is administered at a dose of less than 8 mg. In embodiments, the megestrol acetate is administered at a dose of less than 7 mg. In embodiments, the megestrol acetate is administered at a dose of less than 6 mg. In embodiments, the megestrol acetate is administered at a dose of less than 5 mg. In embodiments, the megestrol acetate is administered at a dose of less than 4 mg. In embodiments, the megestrol acetate is administered at a dose of less than 3 mg. In embodiments, the megestrol acetate is administered at a dose of less than 2 mg. In embodiments, the megestrol acetate is administered at a dose of less than 1 mg. In embodiments, the megestrol acetate is administered at a dose of at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg, but less than an amount indicated above. In embodiments, the megestrol acetate is administered at a dose of at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg. In embodiments, the megestrol acetate is administered at a dose of at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg, but less than 300 mg, 250 mg, 200 mg, 150 mg, or 100 mg.

In embodiments, the megestrol acetate is administered (e.g., at a dose disclosed herein or another dose) at least 1, 2, 3, 4, or 5 times per day, per week, or per month. In embodiments, the megestrol acetate is administered (e.g., at a dose disclosed herein or another dose) 1, 2, 3, 4, or 5 times per day, per week, or per month. In embodiments, the megestrol acetate is administered (e.g., at a dose disclosed herein or another dose) about 1, 2, 3, 4, or 5 times per day, per week, or per month. In embodiments, the megestrol acetate is administered once per day. In embodiments, the megestrol acetate is administered twice per day.

In embodiments, the megestrol acetate is administered orally.

In embodiments, the pterostilbene or pharmaceutically acceptable salt thereof and the megestrol or pharmaceutically acceptable salt thereof are administered to the subject in a single pharmaceutical composition.

In embodiments, the pterostilbene or pharmaceutically acceptable salt thereof and the megestrol or pharmaceutically acceptable salt thereof are administered to the subject in separate pharmaceutical compositions.

In embodiments, the pterostilbene or pharmaceutically acceptable salt thereof and the megestrol or pharmaceutically acceptable salt thereof are administered daily.

In embodiments, the therapeutically effective amount is effective to synergistically reduce tumor volume in the subject.

In embodiments, treating the subject includes reducing the volume of a tumor in the subject.

In embodiments, the subject is a male subject.
In embodiments, the subject is a female subject.
In embodiments, the subject does not have cancer.
In embodiments, the subject is about 20, 25, 30, 35, 40, 45, 50, 55, 65, 70, 75, or 80 years old.

In embodiments, the subject is at risk of developing cancer. In embodiments, the subject is at risk of developing breast cancer. In embodiments, the subject is at risk of developing endometrial cancer. Non-limiting examples of risk factors for endometrial cancer include: obesity, administration of unopposed estrogen therapy, nulliparity, increasing age, tamoxifen use, Lynch syndrome, early menarche, polycystic ovarian syndrome (PCOS), chronic anovulation, diabetes mellitus, estrogen-secreting tumors, Cowden syndrome, and family history of endometrial/ovarian/breast or colon cancer. In embodiments, the subject who is at risk of developing endometrial cancer is obese. In embodiments, the subject who is at risk of developing endometrial cancer has received unopposed estrogen therapy (estrogen therapy alone without progesterone). In embodiments, the subject who is at risk of developing endometrial cancer has nulliparity. In embodiments, the subject who is at risk of developing endometrial cancer is at least about 40, 45, 50, 55, 65, 70, 75, or 80 years old. In embodiments, the subject who is at risk of developing endometrial cancer has been administered tamoxifen. In embodiments, the subject who is at risk of developing endometrial cancer has Lynch syndrome, or at least 1 or 2 grandparents, parents, aunts, uncles, cousins (e.g., first or second cousins), siblings, nieces, nephews, or children who have Lynch syndrome. In embodiments, the subject who is at risk of developing endometrial cancer has Lynch syndrome. In embodiments, the subject who is at risk of developing endometrial cancer has early menarche. In embodiments, the subject who is at risk of developing endometrial cancer has PCOS. In embodiments, the subject who is at risk of developing endometrial cancer has chronic anovulation. In embodiments, the subject who is at risk of developing endometrial cancer has diabetes mellitus. In embodiments, the subject who is at risk of developing endometrial cancer has an estrogen-secreting tumor. In embodiments, the subject who is at risk of developing endometrial cancer has Cowen syndrome, or at least 1 or 2 grandparents, parents, aunts, uncles, cousins (e.g., first or second cousins), siblings, nieces, nephews, or children who have Cowen syndrome. In embodiments, the subject who is at risk of developing endometrial cancer has Cowen syndrome. In embodiments, the subject who is at risk of developing endometrial cancer has at least at least 1 or 2 grandparents, parents, aunts, uncles, cousins (e.g., first or second cousins), siblings, nieces, nephews, or children who have been diagnosed with endometrial cancer. In embodiments, the subject who is at risk of developing endometrial cancer has at least 1 or 2 grandparents, parents, aunts, uncles, cousins (e.g., first or second cousins), siblings, nieces, nephews, or children who have been diagnosed with ovarian cancer. In embodiments, the subject who is at risk of developing endometrial cancer has at least 1 or 2 grandparents, parents, aunts, uncles, cousins (e.g., first or second cousins), siblings, nieces, nephews, or children who have been diagnosed with breast cancer. In embodiments, the subject who is at risk of developing endometrial cancer has at least 1 or 2 grandparents, parents, aunts, uncles, cousins (e.g., first or second cousins), siblings, nieces, nephews, or children who have been diagnosed with colon cancer.

In embodiments, the subject has a hyperplasia.

In embodiments, the subject has an endometrial hyperplasia. Non-limiting descriptions regarding endometrial hyperplasia are provided in Giuntoli and Zacur (2014) Management of endometrial hyperplasia, UpToDate, available from www.uptodate.com/contents/management-of-endometrial-hyperplasia. In embodiments, the subject has simple without atypia endometrial hyperplasia. In embodiments, the subject has complex without atypia endometrial hyperplasia. In embodiments, the subject has simple with atypia endometrial hyperplasia. In embodiments, the subject has complex with atypia endometrial hyperplasia.

In embodiments, the subject has an endometrial glandular dysplasia. In embodiments, the subject has endometrial intraepithelial neoplasia. In embodiments, the subject has endometrial intraepithelial carcinoma.

In embodiments, the subject has breast cancer.
In embodiments, the subject has endometrial cancer.
In embodiments, the subject is post-menopausal.
In embodiments, the subject is pre-menopausal.
In embodiments, the subject is obese. In embodiments, the subject is post-menopausal and obese.

In embodiments, the subject has polycystic ovarian syndrome. In embodiments, the subject is pre-menopausal and has polycystic ovarian syndrome.

In embodiments, the subject has Lynch syndrome. In embodiments, the subject has Cowden syndrome.

In embodiments, the subject has been administered tamoxifen.

In embodiments, the subject has previously been administered radiotherapy to the pelvis.

In embodiments, the subject has previously been diagnosed with ovarian cancer.

In embodiments, the subject has previously been diagnosed with an ovarian granulosa cell tumor or a thecoma. In embodiments, the subject has previously been diagnosed with an ovarian granulosa cell tumor. In embodiments, the subject has previously been diagnosed with a thecoma.

In embodiments, the subject has a mutation in or altered expression of an ARID1A, CTNNB1, FGFR2, KRAS, PIK3R1, TP53, PTEN, PPP2R1A, PIK3CA, PIK3R1, STK15, CCNE1, ERBB2, or CCND1 gene or any combination of 1, 2, 3, 4, 5, 6, 7, 8, 9, 10, 11, 12, 13, or 14 thereof. In embodiments, the subject has a mutation in or altered expression of an ARID1A gene. In embodiments, the subject has a mutation in or altered expression of a CTNNB1 gene. In embodiments, the subject has a mutation in or altered expression of a FGFR2 gene. In embodiments, the subject has a mutation in or altered expression of a KRAS gene. In embodiments, the subject has a mutation in or altered expression of a PIK3R1 gene. In embodiments, the subject has a mutation in or altered expression of a TP53 gene. In embodiments, the subject has a mutation in or altered expression of a PTEN gene. In embodiments, the subject has a mutation in or altered expression of a PPP2R1A gene. In embodiments, the subject has a mutation in or altered expression of a PIK3CA gene. In embodiments, the subject has a mutation in or altered expression of a PIK3R1 gene. In embodiments, the subject has a mutation in or altered expression of a STK15 gene. In embodiments, the subject has a mutation in or altered expression of a CCNE1 gene. In embodiments, the subject has a mutation in or altered expression of an ERBB2 gene. In embodiments, the subject has a mutation in or altered expression of a CCND1 gene.

In embodiments, the subject has a mutation in an ARID1A, CTNNB1, FGFR2, KRAS, PIK3R1, TP53, PTEN, PPP2R1A, PIK3CA, PIK3R1, STK15, CCNE1, ERBB2, or CCND1 gene or any combination of 1, 2, 3, 4, 5, 6, 7, 8, 9, 10, 11, 12, 13, or 14 thereof. In embodiments, the subject has a mutation in an ARID1A gene. In embodiments, the subject has a mutation in a CTNNB1 gene. In embodiments, the subject has a mutation in a FGFR2 gene. In embodiments, the subject has a mutation in a KRAS gene. In embodiments, the subject has a mutation in a PIK3R1 gene. In embodiments, the subject has a mutation in a TP53 gene. In embodiments, the subject has a mutation in a PTEN gene. In embodiments, the subject has a mutation in a PPP2R1A gene. In embodiments, the subject has a mutation in a PIK3CA gene. In embodiments, the subject has a mutation in a PIK3R1 gene. In embodiments, the subject has a mutation in a STK15 gene. In embodiments, the subject has a mutation in a CCNE1 gene. In embodiments, the subject has a mutation in an ERBB2 gene. In embodiments, the subject has a mutation in a CCND1 gene.

In embodiments, the subject has altered expression of an ARID1A, CTNNB1, FGFR2, KRAS, PIK3R1, TP53, PTEN, PPP2R1A, PIK3CA, PIK3R1, STK15, CCNE1, ERBB2, or CCND1 gene or any combination of 1, 2, 3, 4, 5, 6, 7, 8, 9, 10, 11, 12, 13, or 14 thereof. In embodiments, the subject has altered expression of an ARID1A gene. In embodiments, the subject has altered expression of a CTNNB1 gene. In embodiments, the subject has altered expression of a FGFR2 gene. In embodiments, the subject has altered expression of a KRAS gene. In embodiments, the subject has altered expression of a PIK3R1 gene. In embodiments, the subject has altered expression of a TP53 gene. In embodiments, the subject has altered expression of a PTEN gene. In embodiments, the subject has altered expression of a PPP2R1A gene. In embodiments, the subject has altered expression of a PIK3CA gene. In embodiments, the subject has altered expression of a PIK3R1 gene. In embodiments, the subject has altered expression of a STK15 gene. In embodiments, the subject has altered expression of a CCNE1 gene. In embodiments, the subject has altered expression of an ERBB2 gene. In embodiments, the subject has altered expression of a CCND1 gene.

In embodiments, the subject has reduced expression of a MLH1, RASSF1A, SPRY2, or CDKN2A gene. In embodiments, the subject has reduced expression of a MLH1 gene. In embodiments, the subject has reduced expression of a RASSF1A gene. In embodiments, the subject has reduced expression of a SPRY2 gene. In embodiments, the subject has reduced expression of a CDKN2A gene.

In embodiments, the endometrial cancer is Type I or Type II endometrial cancer. In embodiments, the endometrial cancer is Type I endometrial cancer. In embodiments, the endometrial cancer is Type II endometrial cancer. In embodiments, Type I endometrial cancer typically arises from complex atypical hyperplasia and is frequently pathogenetically linked to unopposed estrogenic stimulation. In embodiments, Type II endometrial cancer typically develops from atrophic endometrium and is not linked to hormonally driven pathogenesis.

In embodiments, the endometrial cancer is a carcinoma, an adenocarcinoma, a carcinosarcoma, or a mesenchymal tumor. In embodiments, the endometrial cancer is a carcinoma. In embodiments, the endometrial cancer is an adenocarcinoma. In embodiments, the endometrial cancer is a carcinosarcoma. In embodiments, the endometrial cancer is a mesenchymal tumor.

In embodiments, the endometrial cancer has adenosquamous histology with ER-α expression.

In embodiments, the endometrial cancer is endometroid, serous, or clear-cell endometrial cancer. In embodiments, the endometrial cancer is endometroid endometrial cancer. In embodiments, the endometrial cancer is serous endometrial cancer. In embodiments, the endometrial cancer is clear-cell endometrial cancer. In embodiments, the endometrial cancer is mucinous histology endometrial cancer. In embodiments, the endometrial cancer is a mixed histology endometrial cancer. In embodiments, the endometrial cancer is an undifferentiated histology endometrial cancer. In embodiments, mucinous is uncommon, but can occur. In embodiments, not uncommonly, patients have mixed histologies (a combination of any of the above two or more histologies) within the same tumor. Undifferentiated endometrial cancer is a very aggressive, though rare subtype.

In embodiments, the endometrial cancer is an endometrioid adenocarcinoma, an endometrioid carcinoma, a serous carcinoma, a clear-cell carcinoma, a mucinous carcinoma, a mixed or undifferentiated carcinoma, a squamous cell carcinoma, a transitional cell carcinoma, or an endometrial stromal sarcoma. In embodiments, the endometrial cancer is an endometrioid adenocarcinoma. In embodiments, the endometrial cancer is an endometrioid carcinoma. In embodiments, the endometrial cancer is a serous carcinoma. In embodiments, the endometrial cancer is a clear-cell carcinoma. In embodiments, the endometrial cancer is a mucinous carcinoma. In embodiments, the endometrial cancer is a mixed carcinoma. In embodiments, the endometrial cancer is an undifferentiated carcinoma. In embodiments, the endometrial cancer is a squamous cell carcinoma. In embodiments, the endometrial cancer is a transitional cell carcinoma. In embodiments, the endometrial cancer is an endometrial stromal sarcoma.

In embodiments, the endometrial cancer is recurrent endometrial cancer.

In embodiments, the endometrial cancer is staged using the 2009 International Federation of Gynaecology and Obstetrics staging system. This system is described in Pecorelli S: Revised FIGO staging for carcinoma of the vulva, cervix, and endometrium. Int J Gynaecol Obstet 105 (2): 103-4, 2009, the entire content of which is incorporated herein by reference. In embodiments, the endometrial cancer is Stage 0, Stage IA, IB, II, IIIA, IIIB, IIIC1, IIIC2, IVA or IVB endometrial cancer. In embodiments, the endometrial cancer is Stage 0 endometrial cancer. In embodiments, the endometrial cancer is Stage IA endometrial cancer. In embodiments, the endometrial cancer is Stage IB endometrial cancer. In embodiments, the endometrial cancer is Stage II endometrial cancer. In embodiments, the endometrial cancer is Stage IIIA endometrial cancer. In embodiments, the endometrial cancer is Stage IIIB endometrial cancer. In embodiments, the endometrial cancer is Stage IIIC1 endometrial cancer. In embodiments, the endometrial cancer is Stage IIIC2 endometrial cancer. In embodiments, the endometrial cancer is Stage IVA endometrial cancer. In embodiments, the endometrial cancer is Stage IVB endometrial cancer.

Stage 0 endometrial cancer is referred to as carcinoma in situ, and includes a group or population of abnormal cells that are not cancer cells. In embodiments, Stage IA endometrial cancer is a tumor that is confined to the uterus with less than half myometrial invasion. In embodiments, Stage IB endometrial cancer is a tumor that is confined to the uterus with more than half myometrial invasion. In embodiments, Stage II endometrial cancer is a tumor that involves the uterus and the cervical stroma. In embodiments, Stage IIIA endometrial cancer is a tumor that cancer is a tumor that invades serosa or adnexa. In embodiments, Stage IIIB endometrial cancer is endometrial cancer that has vaginal and/or parametrial involvement. In embodiments, Stage IIIC1 endometrial cancer is endometrial cancer that has pelvic lymph node involvement. In embodiments, Stage IIIC2 endometrial cancer is endometrial cancer that has para-aortic lymph node involvement, with or without pelvic node involvement. In embodiments, Stage IVA endometrial cancer is a tumor that invades bladder mucosa and/or bowel mucosa. In embodiments, Stage IVB endometrial cancer is endometrial cancer with distant metastases including abdominal metastases and/or inguinal lymph nodes.

In embodiments, the subject has not received a hysterectomy.

In embodiments, the subject has not been previously administered radiation therapy or a chemotherapeutic agent. In embodiments, the subject has not been previously administered radiation therapy. In embodiments, the subject has not been previously administered a chemotherapeutic agent.

In embodiments, the subject has previously been administered megestrol acetate without pterostilbene.

In embodiments, the cancer has progressed after a previous administration of megestrol acetate without pterostilbene.

In embodiments, the subject has previously been administered pterostilbene without megestrol acetate.

In embodiments, the cancer has progressed after a previous administration of pterostilbene without megestrol acetate.

In embodiments, the subject has previously been administered a chemotherapeutic agent other than megestrol acetate or pterostilbene.

In embodiments, the cancer has progressed after administration of a chemotherapeutic agent other than megestrol acetate or pterostilbene.

In embodiments, the subject has previously been administered a taxane, an anthracycline, or a platin. In embodiments, the subject has previously been administered a taxane. In embodiments, the subject has previously been administered an anthracycline. In embodiments, the subject has previously been administered a platin.

In embodiments, the subject has previously been administered paclitaxel, docetaxel, doxorubicin, cisplatin, or carboplatin. In embodiments, the subject has previously been administered paclitaxel. In embodiments, the subject has previously been administered docetaxel. In embodiments, the subject has previously been administered doxorubicin. In embodiments, the subject has previously been administered cisplatin. In embodiments, the subject has previously been administered carboplatin. In embodiments, the subject has previously been administered a doxorubicin hydrochloride liposome injection (e.g., Doxil®). In embodiments, the subject has previously been administered bevacizumab (e.g., Avastin®). In embodiments, the subject has previously been administered temsirolimus. In embodiments, the subject has previously been administered ifosfamide. In embodiments, the subject has previously been administered topotecan.

In embodiments, the subject has previously been administered hydroxyprogesterone caproate, letrozole, or medroxyprogesterone. In embodiments, the subject has previously been administered hydroxyprogesterone caproate. In embodiments, the subject has previously been administered letrozole. In embodiments, the subject has previously been administered medroxyprogesterone.

In an aspect, provided herein is a method of increasing the likelihood that a subject will respond to megestrol acetate treatment for cancer, including administering pterostilbene or a pharmaceutically acceptable salt thereof to the subject.

In embodiments, the subject has not been administered megestrol acetate.

In embodiments, the subject has a tumor, the subject has been administered megestrol acetate, and the volume of the tumor has not decreased since the subject was administered megestrol acetate.

In an aspect, provided herein is a method of increasing the likelihood that a subject will respond to megestrol or a pharmaceutically acceptable salt thereof treatment for cancer, including administering pterostilbene or a pharmaceutically acceptable salt thereof to the subject.

In embodiments, the subject has not been administered megestrol or a pharmaceutically acceptable salt thereof.

In embodiments, the subject has a tumor, wherein the subject has been administered megestrol or a pharmaceutically acceptable salt thereof, and wherein the volume of the tumor has not decreased since the subject was administered megestrol or a pharmaceutically acceptable salt thereof.

In an aspect, provided herein is a method of increasing the likelihood that a subject will respond to pterostilbene treatment for cancer, including administering megestrol acetate to the subject.

In embodiments, the subject has not been administered pterostilbene.

In embodiments, the subject has a tumor, the subject has been administered pterostilbene, and the volume of the tumor has not decreased since the subject was administered pterostilbene.

In an aspect, provided herein is a method of increasing the likelihood that a subject will respond to pterostilbene or a pharmaceutically acceptable salt thereof treatment for cancer, including administering megestrol or a pharmaceutically acceptable salt thereof to the subject.

In embodiments, the subject has not been administered pterostilbene or a pharmaceutically acceptable salt thereof.

In embodiments, the subject has a tumor, the subject has been administered pterostilbene or a pharmaceutically acceptable salt thereof, and the volume of the tumor has not decreased since the subject was administered pterostilbene or a pharmaceutically acceptable salt thereof.

In an aspect, provided herein is a method of treating cancer in a subject who has previously received a first amount of megestrol acetate, including administering (i) a second amount of megestrol acetate that is less than said first amount; and (ii) an amount of pterostilbene.

In an aspect, provided herein is a method of treating cancer in a subject who has previously received a first amount of megestrol or a pharmaceutically acceptable salt thereof, including administering (i) a second amount of megestrol or a pharmaceutically acceptable salt thereof that is less than said first amount; and (ii) an amount of pterostilbene or a pharmaceutically acceptable salt thereof.

In an aspect, provided herein is a method of treating cancer in a subject who has previously received a first amount of pterostilbene, including administering (i) a second amount of pterostilbene that is less than said first amount; and (ii) an amount of megestrol acetate.

In an aspect, provided herein is a method of treating cancer in a subject who has previously received a first amount of pterostilbene or a pharmaceutically acceptable salt thereof, including administering (i) a second amount of pterostilbene or a pharmaceutically acceptable salt thereof that is less than said first amount; and (ii) an amount of megestrol or a pharmaceutically acceptable salt thereof.

Pharmaceutical Compositions

In an aspect, provided herein is a pharmaceutical composition comprising a therapeutically effective amount of (i) a stilbenoid compound (e.g., resveratrol, isorhapontigenin, piceatannol, oxyresveratrol, rhapontigenin, gnetol, or pterostilbene) and a progestin (e.g., progesterone, megestrol, megestrol acetate, levonorgestrel, medroxyprogesterone, medoxyprogesterone acetate, norethindrone, and norethindrone acetate), and (ii) a pharmaceutically acceptable excipient. In embodiments, the pharmaceutical composition consists essentially of a therapeutically effective amount of (i) a stilbenoid compound (e.g., resveratrol, isorhapontigenin, piceatannol, oxyresveratrol, rhapontigenin, gnetol, or pterostilbene) and a progestin (e.g., progesterone, megestrol, megestrol acetate, levonorgestrel, medroxyprogesterone, medoxyprogesterone acetate, norethindrone, and norethindrone acetate), and (ii) a pharmaceutically acceptable excipient. In embodiments, the pharmaceutical composition consists of a therapeutically effective amount of (i) a stilbenoid compound (e.g., resveratrol, isorhapontigenin, piceatannol, oxyresveratrol, rhapontigenin, gnetol, or pterostilbene) and a progestin (e.g., progesterone, megestrol, megestrol acetate, levonorgestrel, medroxyprogesterone, medoxyprogesterone acetate, norethindrone, and norethindrone acetate), and (ii) a pharmaceutically acceptable excipient. In embodiments, the composition does not comprise another active agent that is used to kill or inhibit the proliferation of cancer cells is administered to the subject.

In embodiments, the stilbenoid compound is resveratrol, isorhapontigenin, piceatannol, oxyresveratrol, rhapontigenin, gnetol, pterostilbene, or a pharmaceutically acceptable salt thereof. In embodiments, the stilbenoid is resveratrol or a pharmaceutically acceptable salt thereof. In embodiments, the stilbenoid is isorhapontigenin or a pharmaceutically acceptable salt thereof. In embodiments, the stilbenoid is piceatannol or a pharmaceutically acceptable salt thereof. In embodiments, the stilbenoid is oxyresveratrol or a pharmaceutically acceptable salt thereof. In embodiments, the stilbenoid is rhapontigenin or a pharmaceutically acceptable salt thereof. In embodiments, the stilbenoid is gnetol or a pharmaceutically acceptable salt thereof. In embodiments, the stilbenoid is pterostilbene or a pharmaceutically acceptable salt thereof.

In embodiments, the progestin is progesterone. In embodiments, the progestin is medroxyprogesterone or a pharmaceutically acceptable salt thereof (e.g., medoxyprogesterone acetate), norethindrone or a pharmaceutically acceptable salt thereof (e.g., norethindrone acetate), micronized progesterone, depot MPA, levonorgestrel, or megestrol. In embodiments, the progestin is medroxyprogesterone or a pharmaceutically acceptable salt thereof (e.g., medoxyprogesterone acetate). In embodiments, the progestin is micronized progesterone. In embodiments, the progestin is depot MPA. In embodiments, the progestin is norethindrone acetate. In embodiments, the progestin is levonorgestrel. In embodiments, the levonorgestrel is in a levonorgestrel-releasing intrauterine device (e.g., LNg20 or Mirena®). In embodiments, the progestin is megestrol or a pharmaceutically acceptable salt thereof (e.g., megestrol acetate). In embodiments, a progestin binds to nPR.

In an aspect, provided herein is a pharmaceutical composition that comprises a therapeutically effective amount of (i) pterostilbene or a pharmaceutically acceptable salt thereof and megestrol or a pharmaceutically acceptable salt thereof, and (ii) a pharmaceutically acceptable excipient. In embodiments, the pharmaceutical composition consists essentially of a therapeutically effective amount of (i) pterostilbene or a pharmaceutically acceptable salt thereof and megestrol or a pharmaceutically acceptable salt thereof, and (ii) a pharmaceutically acceptable excipient. In embodiments, the pharmaceutical composition consists of a therapeutically effective amount of (i) pterostilbene or a pharmaceutically acceptable salt thereof and megestrol or a pharmaceutically acceptable salt thereof, and (ii) a pharmaceutically acceptable excipient.

In embodiments, the therapeutically effective amount is a combined synergistic amount.

In embodiments, the pharmaceutical composition includes less than 280 mg pterostilbene. In embodiments, the pharmaceutical composition includes less than 270 mg pterostilbene. In embodiments, the pharmaceutical composition includes less than 260 mg pterostilbene. In embodiments, the pharmaceutical composition includes less than 250 mg pterostilbene. In embodiments, the pharmaceutical composition includes less than 240 mg pterostilbene. In embodiments, the pharmaceutical composition includes less than 230 mg pterostilbene. In embodiments, the pharmaceutical composition includes less than 220 mg pterostilbene. In embodiments, the pharmaceutical composition includes less than 210 mg pterostilbene. In embodiments, the pharmaceutical composition includes less than 200 mg pterostilbene. In embodiments, the pharmaceutical composition includes less than 190 mg pterostilbene. In embodiments, the pharmaceutical composition includes less than 180 mg pterostilbene. In embodiments, the pharmaceutical composition includes less than 170 mg pterostilbene. In embodiments, the pharmaceutical composition includes less than 160 mg pterostilbene. In embodiments, the pharmaceutical composition includes less than 150 mg pterostilbene. In embodiments, the pharmaceutical composition includes less than 140 mg pterostilbene. In embodiments, the pharmaceutical composition includes less than 130 mg pterostilbene. In embodiments, the pharmaceutical composition includes less than 120 mg pterostilbene. In embodiments, the pharmaceutical composition includes less than 110 mg pterostilbene. In embodiments, the pharmaceutical composition includes less than 100 mg pterostilbene. In embodiments, the pharmaceutical composition includes less than 90 mg pterostilbene. In embodiments, the pharmaceutical composition includes less than 80 mg pterostilbene. In embodiments, the pharmaceutical composition includes less than 75 mg pterostilbene. In embodiments, the pharmaceutical composition includes less than 70 mg pterostilbene. In embodiments, the pharmaceutical composition includes less than 65 mg pterostilbene. In embodiments, the pharmaceutical composition includes less than 60 mg pterostilbene. In embodiments, the pharmaceutical composition includes less than 55 mg pterostilbene. In embodiments, the pharmaceutical composition includes less than 50 mg pterostilbene. In embodiments, the pharmaceutical composition includes less than 48 mg pterostilbene. In embodiments, the pharmaceutical composition includes less than 46 mg pterostilbene. In embodiments, the pharmaceutical composition includes less than 44 mg pterostilbene. In embodiments, the pharmaceutical composition includes less than 42 mg pterostilbene. In embodiments, the pharmaceutical composition includes less than 40 mg pterostilbene. In embodiments, the pharmaceutical composition includes less than 38 mg pterostilbene. In embodiments, the pharmaceutical composition includes less than 36 mg pterostilbene. In embodiments, the pharmaceutical composition includes less than 34 mg pterostilbene. In embodiments, the pharmaceutical composition includes less than 32 mg pterostilbene. In embodiments, the pharmaceutical composition includes less than 30 mg pterostilbene. In embodiments, the pharmaceutical composition includes less than 28 mg pterostilbene. In embodiments, the pharmaceutical composition includes less than 26 mg pterostilbene. In embodiments, the pharmaceutical composition includes less than 24 mg pterostilbene. In embodiments, the pharmaceutical composition includes less than 22 mg pterostilbene. In embodiments, the pharmaceutical composition includes less than 20 mg pterostilbene. In embodiments, the pharmaceutical composition includes at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg pterostilbene, but less than an amount indicated above. In embodiments, the pharmaceutical composition includes at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg pterostilbene. In embodiments, the pharmaceutical composition includes at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg, but less than 300 mg, 250 mg, 200 mg, 150 mg, or 100 mg pterostilbene.

In embodiments, the pharmaceutical composition includes 40 mg to 800 mg megestrol acetate. In embodiments, the pharmaceutical composition includes 40 mg to 750 mg megestrol acetate. In embodiments, the pharmaceutical composition includes 40 mg to 700 mg megestrol acetate. In embodiments, the pharmaceutical composition includes 40 mg to 650 mg megestrol acetate. In embodiments, the pharmaceutical composition includes 40 mg to 600 mg megestrol acetate. In embodiments, the pharmaceutical composition includes 40 mg to 550 mg megestrol acetate. In embodiments, the pharmaceutical composition includes 40 mg to 500 mg megestrol acetate. In embodiments, the pharmaceutical composition includes 40 mg to 450 mg megestrol acetate. In embodiments, the pharmaceutical composition includes 40 mg to 400 mg megestrol acetate. In embodiments, the pharmaceutical composition includes 40 mg to 350 mg megestrol acetate. In embodiments, the pharmaceutical composition includes 40 mg to 320 mg megestrol acetate. In embodiments, the pharmaceutical composition includes 45 mg to 320 mg megestrol acetate. In embodiments, the pharmaceutical composition includes 50 mg to 320 mg megestrol acetate. In embodiments, the pharmaceutical composition includes 60 mg to 320 mg megestrol acetate. In embodiments, the pharmaceutical composition includes 70 mg to 320 mg megestrol acetate. In embodiments, the pharmaceutical composition includes 80 mg to 320 mg megestrol acetate. In embodiments, the pharmaceutical composition includes 90 mg to 320 mg megestrol acetate. In embodiments, the pharmaceutical composition includes 100 mg to 320 mg megestrol acetate. In embodiments, the pharmaceutical composition includes 110 mg to 320 mg megestrol acetate. In embodiments, the pharmaceutical composition includes 120 mg to 320 mg megestrol acetate. In embodiments, the pharmaceutical composition includes 130 mg to 320 mg megestrol acetate. In embodiments, the pharmaceutical composition includes 140 mg to 320 mg megestrol acetate. In embodiments, the pharmaceutical composition includes 150 mg to 320 mg megestrol acetate. In embodiments, the pharmaceutical composition includes 160 mg to 320 mg megestrol acetate. In embodiments, the pharmaceutical composition includes 170 mg to 320 mg megestrol acetate. In embodiments, the pharmaceutical composition includes 180 mg to 320 mg megestrol acetate. In embodiments, the pharmaceutical composition includes 190 mg to 320 mg megestrol acetate. In embodiments, the pharmaceutical composition includes 200 mg to 320 mg megestrol acetate. In embodiments, the pharmaceutical composition includes 210 mg to 320 mg megestrol acetate. In embodiments, the pharmaceutical composition includes 220 mg to 320 mg megestrol acetate. In embodiments, the pharmaceutical composition includes 230 mg to 320 mg megestrol acetate. In embodiments, the pharmaceutical composition includes 240 mg to 320 mg megestrol acetate. In embodiments, the pharmaceutical composition includes 250 mg to 320 mg megestrol acetate. In embodiments, the pharmaceutical composition includes 260 mg to 320 mg megestrol acetate. In embodiments, the pharmaceutical composition includes 270 mg to 320 mg megestrol acetate. In embodiments, the pharmaceutical composition includes 280 mg to 320 mg megestrol acetate. In embodiments, the pharmaceutical composition includes 290 mg to 320 mg megestrol acetate. In embodiments, the pharmaceutical composition includes 300 mg to 320 mg megestrol acetate. In embodiments, the pharmaceutical composition includes 310 mg to 320 mg megestrol acetate. In embodiments, the pharmaceutical composition includes 310 mg to 315 mg megestrol acetate.

In embodiments, the pharmaceutical composition includes 40 mg to 310 mg megestrol acetate. In embodiments, the pharmaceutical composition includes 40 mg to 300 mg megestrol acetate. In embodiments, the pharmaceutical composition includes 40 mg to 290 mg megestrol acetate. In embodiments, the pharmaceutical composition includes 40 mg to 280 mg megestrol acetate. In embodiments, the pharmaceutical composition includes 40 mg to 270 mg megestrol acetate. In embodiments, the pharmaceutical composition includes 40 mg to 260 mg megestrol acetate. In embodiments, the pharmaceutical composition includes 40 mg to 250 mg megestrol acetate. In embodiments, the pharmaceutical composition includes 40 mg to 240 mg megestrol acetate. In embodiments, the pharmaceutical composition includes 40 mg to 230 mg megestrol acetate. In embodiments, the pharmaceutical composition includes 40 mg to 220 mg megestrol acetate. In embodiments, the pharmaceutical composition includes 40 mg to 200 mg megestrol acetate. In embodiments, the pharmaceutical composition includes 40 mg to 190 mg megestrol acetate. In embodiments, the pharmaceutical composition includes 40 mg to 180 mg megestrol acetate. In embodiments, the pharmaceutical composition includes 40 mg to 170 mg megestrol acetate. In embodiments, the pharmaceutical composition includes 40 mg to 160 mg megestrol acetate. In embodiments, the pharmaceutical composition includes 40 mg to 150 mg megestrol acetate. In embodiments, the pharmaceutical composition includes 40 mg to 140 mg megestrol acetate. In embodiments, the pharmaceutical composition includes 40 mg to 130 mg megestrol acetate. In embodiments, the pharmaceutical composition includes 40 mg to 120 mg megestrol acetate. In embodiments, the pharmaceutical composition includes 40 mg to 110 mg megestrol acetate. In embodiments, the pharmaceutical composition includes 40 mg to 100 mg megestrol acetate. In embodiments, the pharmaceutical composition includes 40 mg to 90 mg megestrol acetate. In embodiments, the pharmaceutical composition includes 40 mg to 80 mg megestrol acetate. In embodiments, the pharmaceutical composition includes 40 mg to 70 mg megestrol acetate. In embodiments, the pharmaceutical composition includes 40 mg to 60 mg megestrol acetate. In embodiments, the pharmaceutical composition includes 40 mg to 50 mg megestrol acetate. In embodiments, the pharmaceutical composition includes 40 mg to 45 mg megestrol acetate.

In embodiments, the pharmaceutical composition includes less than 800 mg megestrol acetate. In embodiments, the pharmaceutical composition includes less than 700 mg megestrol acetate. In embodiments, the pharmaceutical composition includes less than 600 mg megestrol acetate. In embodiments, the pharmaceutical composition includes less than 500 mg megestrol acetate. In embodiments, the pharmaceutical composition includes less than 400 mg megestrol acetate. In embodiments, the pharmaceutical composition includes less than 300 mg megestrol acetate. In embodiments, the pharmaceutical composition includes less than 200 mg megestrol acetate. In embodiments, the pharmaceutical composition includes less than 100 mg megestrol acetate. In embodiments, the pharmaceutical composition includes less than 50 mg megestrol acetate. In embodiments, the pharmaceutical composition includes less than 40 mg megestrol acetate. In embodiments, the pharmaceutical composition includes less than 30 mg megestrol acetate. In embodiments, the pharmaceutical composition includes less than 20 mg megestrol acetate. In embodiments, the pharmaceutical composition includes less than 15 mg megestrol acetate. In embodiments, the pharmaceutical composition includes less than 10 mg megestrol acetate. In embodiments, the pharmaceutical composition includes less than 9 mg megestrol acetate. In embodiments, the pharmaceutical composition includes less than 8 mg megestrol acetate. In embodiments, the pharmaceutical composition includes less than 7 mg megestrol acetate. In embodiments, the pharmaceutical composition includes less than 6 mg megestrol acetate. In embodiments, the pharmaceutical composition includes less than 5 mg megestrol acetate. In embodiments, the pharmaceutical composition includes less than 4 mg megestrol acetate. In embodiments, the pharmaceutical composition includes less than 3 mg megestrol acetate. In embodiments, the pharmaceutical composition includes less than 2 mg megestrol acetate. In embodiments, the pharmaceutical composition includes less than 1 mg megestrol acetate. In embodiments, the pharmaceutical composition includes at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg megestrol acetate, but less than an amount indicated above. In embodiments, the pharmaceutical composition includes at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg megestrol acetate. In embodiments, the pharmaceutical composition includes at least 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, or 50 mg, but less than 300 mg, 250 mg, 200 mg, 150 mg, or 100 mg megestrol acetate.

In embodiments, the pharmaceutical composition includes less than 50 mg pterostilbene and less than 40 mg megestrol acetate. In embodiments, the pharmaceutical composition includes less than 50 mg pterostilbene and less than 30 mg megestrol acetate. In embodiments, the pharmaceutical composition includes less than 50 mg pterostilbene and less than 20 mg megestrol acetate. In embodiments, the pharmaceutical composition includes less than 50 mg pterostilbene and less than 15 mg megestrol acetate. In embodiments, the pharmaceutical composition includes less than 50 mg pterostilbene and less than 10 mg megestrol acetate. In embodiments, the pharmaceutical composition includes less than 50 mg pterostilbene and less than 5 mg megestrol acetate. In embodiments, the pharmaceutical composition includes less than 50 mg pterostilbene and less than 1 mg megestrol acetate.

In embodiments, the pharmaceutical composition includes less than 40 mg pterostilbene and less than 40 mg megestrol acetate. In embodiments, the pharmaceutical composition includes less than 40 mg pterostilbene and less than 30 mg megestrol acetate. In embodiments, the pharmaceutical composition includes less than 40 mg pterostilbene and less than 20 mg megestrol acetate. In embodiments, the pharmaceutical composition includes less than 40 mg pterostilbene and less than 15 mg megestrol acetate. In embodiments, the pharmaceutical composition includes less than 40 mg pterostilbene and less than 10 mg megestrol acetate. In embodiments, the pharmaceutical composition includes less than 40 mg pterostilbene and less than 5 mg megestrol acetate. In embodiments, the pharmaceutical composition includes less than 40 mg pterostilbene and less than 1 mg megestrol acetate.

In embodiments, the pharmaceutical composition includes less than 30 mg pterostilbene and less than 40 mg megestrol acetate. In embodiments, the pharmaceutical composition includes less than 30 mg pterostilbene and less than 30 mg megestrol acetate. In embodiments, the pharmaceutical composition includes less than 30 mg pterostilbene and less than 20 mg megestrol acetate. In embodiments, the pharmaceutical composition includes less than 30 mg pterostilbene and less than 15 mg megestrol acetate. In embodiments, the pharmaceutical composition includes less than 30 mg pterostilbene and less than 10 mg megestrol acetate. In embodiments, the pharmaceutical composition includes less than 30 mg pterostilbene and less than 5 mg megestrol acetate. In embodiments, the pharmaceutical composition includes less than 30 mg pterostilbene and less than 1 mg megestrol acetate.

In embodiments, the pharmaceutical composition includes less than 20 mg pterostilbene and less than 40 mg megestrol acetate. In embodiments, the pharmaceutical composition includes less than 20 mg pterostilbene and less than 30 mg megestrol acetate. In embodiments, the pharmaceutical composition includes less than 20 mg pterostilbene and less than 20 mg megestrol acetate. In embodiments, the pharmaceutical composition includes less than 20 mg pterostilbene and less than 15 mg megestrol acetate. In embodiments, the pharmaceutical composition includes less than 20 mg pterostilbene and less than 10 mg megestrol acetate. In embodiments, the pharmaceutical composition includes less than 20 mg pterostilbene and less than 5 mg megestrol acetate. In embodiments, the pharmaceutical composition includes less than 20 mg pterostilbene and less than 1 mg megestrol acetate.

In embodiments, the pharmaceutical composition includes less than 10 mg pterostilbene and less than 40 mg megestrol acetate. In embodiments, the pharmaceutical composition includes less than 10 mg pterostilbene and less than 30 mg megestrol acetate. In embodiments, the pharmaceutical composition includes less than 10 mg pterostilbene and less than 20 mg megestrol acetate. In embodiments, the pharmaceutical composition includes less than 10 mg pterostilbene and less than 15 mg megestrol acetate. In embodiments, the pharmaceutical composition includes less than 10 mg pterostilbene and less than 10 mg megestrol acetate. In embodiments, the pharmaceutical composition includes less than 10 mg pterostilbene and less than 5 mg megestrol acetate. In embodiments, the pharmaceutical composition includes less than 10 mg pterostilbene and less than 1 mg megestrol acetate.

In embodiments, the pharmaceutical composition includes less than 5 mg pterostilbene and less than 40 mg megestrol acetate. In embodiments, the pharmaceutical composition includes less than 5 mg pterostilbene and less than 30 mg megestrol acetate. In embodiments, the pharmaceutical composition includes less than 5 mg pterostilbene and less than 20 mg megestrol acetate. In embodiments, the pharmaceutical composition includes less than 5 mg pterostilbene and less than 15 mg megestrol acetate. In embodiments, the pharmaceutical composition includes less than 5 mg pterostilbene and less than 10 mg megestrol acetate. In embodiments, the pharmaceutical composition includes less than 5 mg pterostilbene and less than 5 mg megestrol acetate. In embodiments, the pharmaceutical composition includes less than 5 mg pterostilbene and less than 1 mg megestrol acetate.

In embodiments, the pharmaceutical composition includes less than 1 mg pterostilbene and less than 40 mg megestrol acetate. In embodiments, the pharmaceutical composition includes less than 1 mg pterostilbene and less than 30 mg megestrol acetate. In embodiments, the pharmaceutical composition includes less than 1 mg pterostilbene and less than 20 mg megestrol acetate. In embodiments, the pharmaceutical composition includes less than 1 mg pterostilbene and less than 15 mg megestrol acetate. In embodiments, the pharmaceutical composition includes less than 1 mg pterostilbene and less than 10 mg megestrol acetate. In embodiments, the pharmaceutical composition includes less than 1 mg pterostilbene and less than 5 mg megestrol acetate. In embodiments, the pharmaceutical composition includes less than 1 mg pterostilbene and less than 1 mg megestrol acetate.

In embodiments, the pharmaceutical composition is in an oral dosage form.

In embodiments, the pharmaceutical composition is in the form of a tablet, a capsule, a suspension, or an aqueous solution. In embodiments, the pharmaceutical composition is in the form of a tablet. In embodiments, the pharmaceutical composition is in the form of a capsule. In embodiments, the pharmaceutical composition is in the form of a suspension. In embodiments, the pharmaceutical composition is in the form of an aqueous solution.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1. The Natural Stilbenoid Pterostilbene Synergizes the Antineoplastic Effects of Megestrol Acetate in Endometrial Cancer Endometrial cancer is the most common gynecologic cancer in the United States and its incidence and mortality has been rising over the past decade. Few treatment options are available for patients with advanced and recurring endometrial cancers. Novel therapies, which are frequently toxic, are difficult to establish in this patient population which tends to be older and plagued by comorbidities such as diabetes mellitus and hypertension. Therefore, novel, non-toxic therapies are urgently needed. Megestrol acetate is a frequently used drug in endometrial cancer patients, however, its response rate is only 20-30%. To enhance the activity of megestrol acetate in endometrial cancer patients, the potential of combining natural supplements with megestrol acetate was explored, and it was found that the addition of the natural antioxidant, pterostilbene, to megestrol acetate resulted in a synergistic inhibition of cancer cell growth in vitro and an enhanced reduction of tumor growth in a xenograft mouse model. In addition, dual treatment led to attenuation of signaling pathways, as well as cell cycle and survival pathways. The results demonstrated for the first time that the anti-tumor activity of megestrol acetate can be enhanced by combining with pterostilbene. The data also indicate that the combination of pterostilbene and megestrol acetate is useful for the treatment of endometrial cancer.

To potentially enhance the activity of megestrol acetate in endometrial cancer patients, non-toxic natural supplements were explored. Recently, the resveratrol analog pterostilbene, a naturally occurring antioxidant primarily found in blueberries, has been shown to possess antitumor activity[17-28]. Pterostilbene has superior bioavailability as compared to Resveratrol, with a favorable safety profile, and appears to act via apoptotic and anti-proliferative mechanisms in multiple solid cancer cells[17,18,29]. Specifically, its effects on cell death and cell cycle alterations have been documented in bladder, lung, and gastric cancer[30-32]. Recent reports suggest that its antioxidant and anticancer effects are mediated by estrogen receptors, as reported in breast cancer and colon cancer[30,33]. To date, the antitumor effects of pterostilbene have not been studied in endometrial cancer, a common estrogen-responsive cancer.

In embodiments, pterostilbene effectively reduces endometrial cancer growth both in vitro and in vivo, and enhances the antitumor activity of megestrol acetate in endometrial cancer. The antiproliferative effect of pterostilbene was tested with and without megestrol acetate in multiple endometrial cancer cells, and their anti-tumor effect was tested in an endometrial cancer xenograft mouse model, while elucidating their effect on multiple growth and survival pathways, including MAPK/ERK and PI3K/AKT pathways. The results introduce pterostilbene as a potential therapeutic adjunct which effectively synergizes the antineoplastic effects of megestrol acetate in endometrial cancer, likely by reducing estrogen receptor expression, inhibiting MAPK/ERK signaling and subsequently suppressing cancer cell growth and survival.

Results

Pterostilbene Inhibits Endometrial Cancer Cell Growth.

To study the anti-tumor activity of pterostilbene in endometrial cancer, its effect was tested on cell growth in two endometrial cancer cell lines, ECC-1, an ER/PR responsive cell line derived from a patient with a well-differentiated endometrial cancer, and HEC-1A, a cell line derived from an endometrial cancer patient with adenosquamous histology with moderate ER-α expression[34-36]. Exponentially growing cells were treated with increasing concentrations of pterostilbene (37.5-300 μm) for 48 h. As shown in FIG. 1, pterostilbene significantly reduced cell viability in a dose-dependent manner, with $IC_{50}$ (concentration for 50% growth inhibition) between 72 and 78 μM. These results indicate that pterostilbene can potently inhibit endometrial cancer cell growth.

Synergistic Effects of Pterostilbene in Combination with Megestrol Acetate.

Figure 2A:
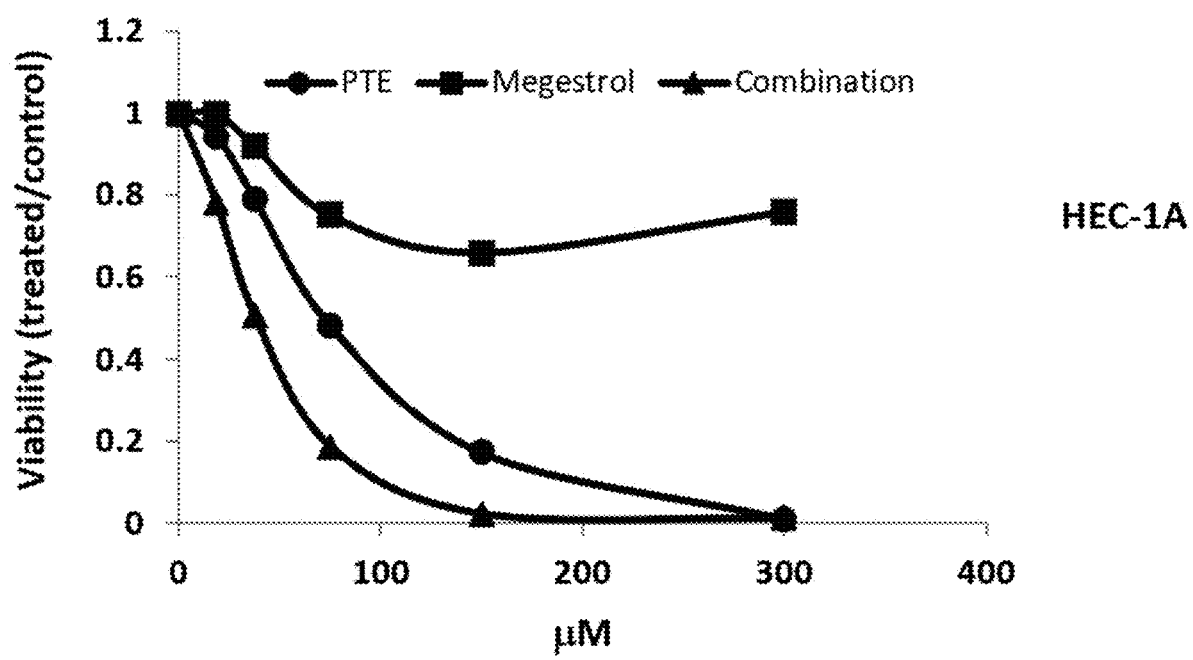
FIGS. 2A-2C. Synergistic effects of Pterostilbene (PTE) in combination with megestrol acetate (which is shortened to "Megestrol" in FIGS. 2A and 2B) in human endometrial cancer cells. HEC-1A (FIG. 2A) and ECC-1 (FIG. 2B) cells were treated with Pterostilbene or megestrol acetate either alone or in combination at various concentrations in a fixed molar ratio 1:1. Cell viability was determined 72 h later.
Figure 2B:
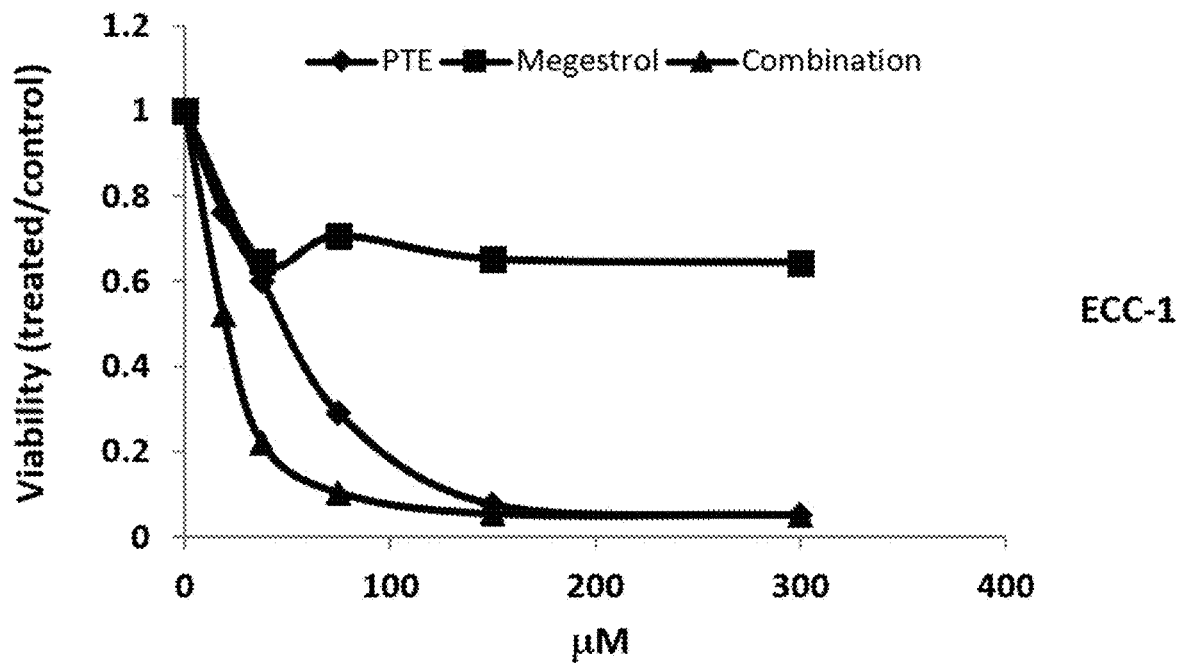
Figure 2C:
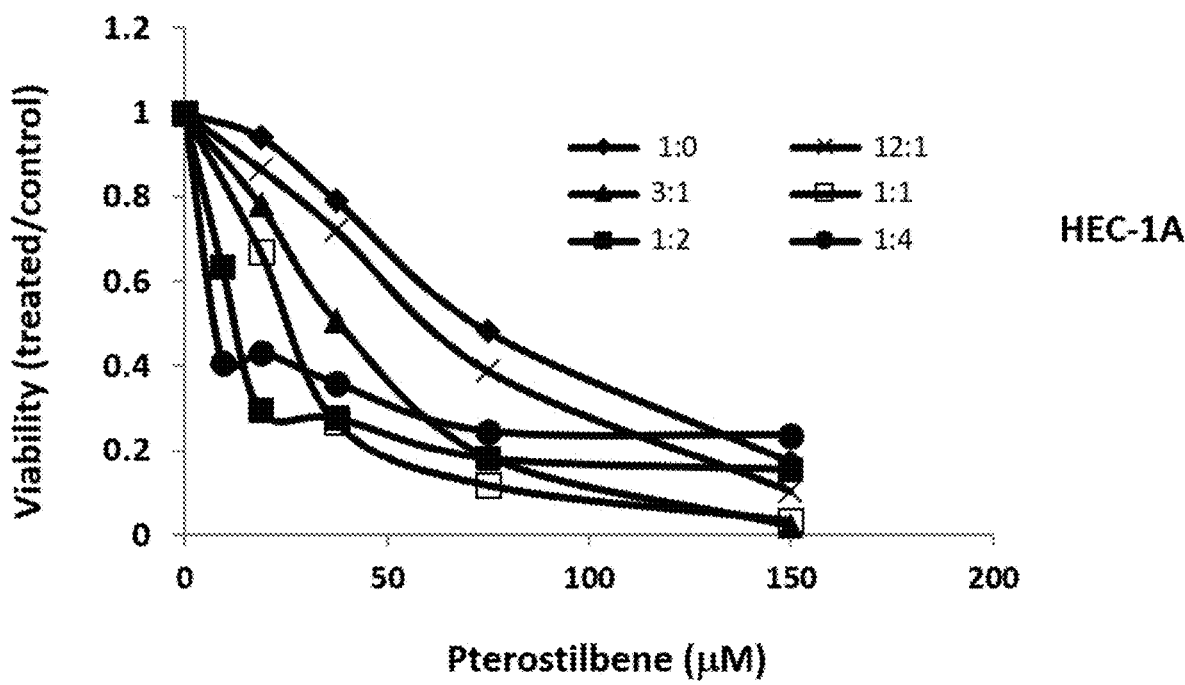

To study the effect of adding pterostilbene to megestrol acetate (optionally referred to as "Megace"), its effect on cell growth was tested in the two endometrial cancer cell lines, ECC-1 and HEC-1A, either alone or in combination at various concentrations in a fixed molar ratio 1:1. Cell viability was determined 72 hours later (FIGS. 2A-2B). The combination index (CI) was determined using the Chou-Talalay method[37]. Evaluation of the synergistic interaction revealed a positive synergistic effect for the combination of pterostilbene and megestrol acetate in both ECC-1 and HEC-1A cells, as shown in Table 1. The synergistic interaction between pterostilbene and megestrol acetate in HEC-1A is additionally depicted in a variety of molar ratios in FIG. 2C and Table 2. The combination treatment produced a strong synergism at each molar ratio. But it appears the combination at 1:1 molar ratio produced stronger synergy and a lower $IC_{50}$ for both agents in the HEC-1A cells.

Combination Treatment of Pterostilbene and Megestrol Acetate Suppresses Cell Survival and Cell Cycle Pathways in Endometrial Cancer Cells.

Figure 3A:
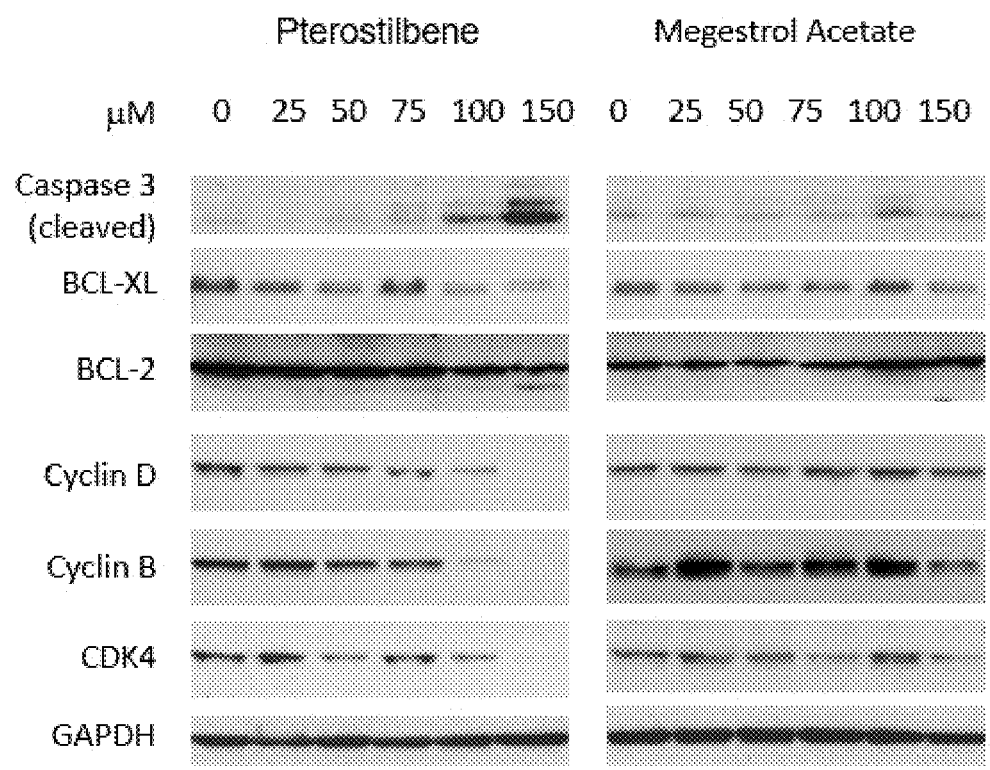
FIGS. 3A-3B. Effect of Pterostilbene (PTE) and megestrol acetate on the expression of cell cycle molecules and cell survival molecules.
Figure 3B:
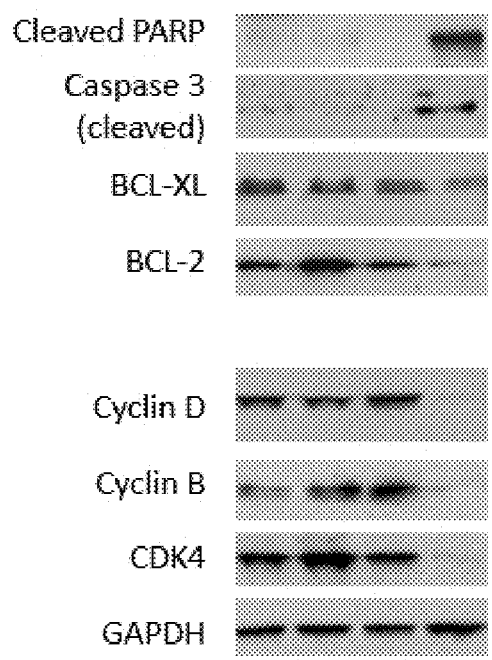

The effect of combined treatment on the expression of proteins involved in cell survival was investigated next. The administration of pterostilbene by itself caused increased cleavage of caspase 3, a molecular marker for apoptosis, and a decrease in BCL-2 and BCL-xl, two proteins for cell survival, in a dose dependent manner (FIG. 3A). Megestrol acetate alone had little effect on the expression of these proteins (FIG. 3A). The combination of pterostilbene and megestrol acetate caused an increase in cleavage of caspase 3 and poly-ADP ribose polymerase (PARP), indicating that more cells underwent apoptosis when pterostilbene was combined with megestrol acetate. Consistent with this result, an enhanced reduction of BCL-2 and BCL-xl was also found in cells treated with both pterostilbene and megestrol acetate (FIG. 3B).

In addition, the effect of pterostilbene and megestrol acetate on cell cycle regulators, such as cyclin D1, cyclin B1 and CDK4, was examined. While pterostilbene alone inhibited the expression of these proteins in a dose dependent manner, megestrol acetate had little impact on these proteins (FIG. 3A). The combination treatment led to an increased inhibition of cyclin D1, cyclin B1 and CDK4 (FIG. 3B). The results demonstrated that addition of pterostilbene to megestrol acetate led to an enhanced inhibition of cell survival and cell cycle progression in endometrial cancer.

Combination Treatment of Pterostilbene and Megestrol Acetate Suppresses MAPK/ERK Signaling and Estrogen Receptor Expression in Endometrial Cancer Cells.

Figure 4A:
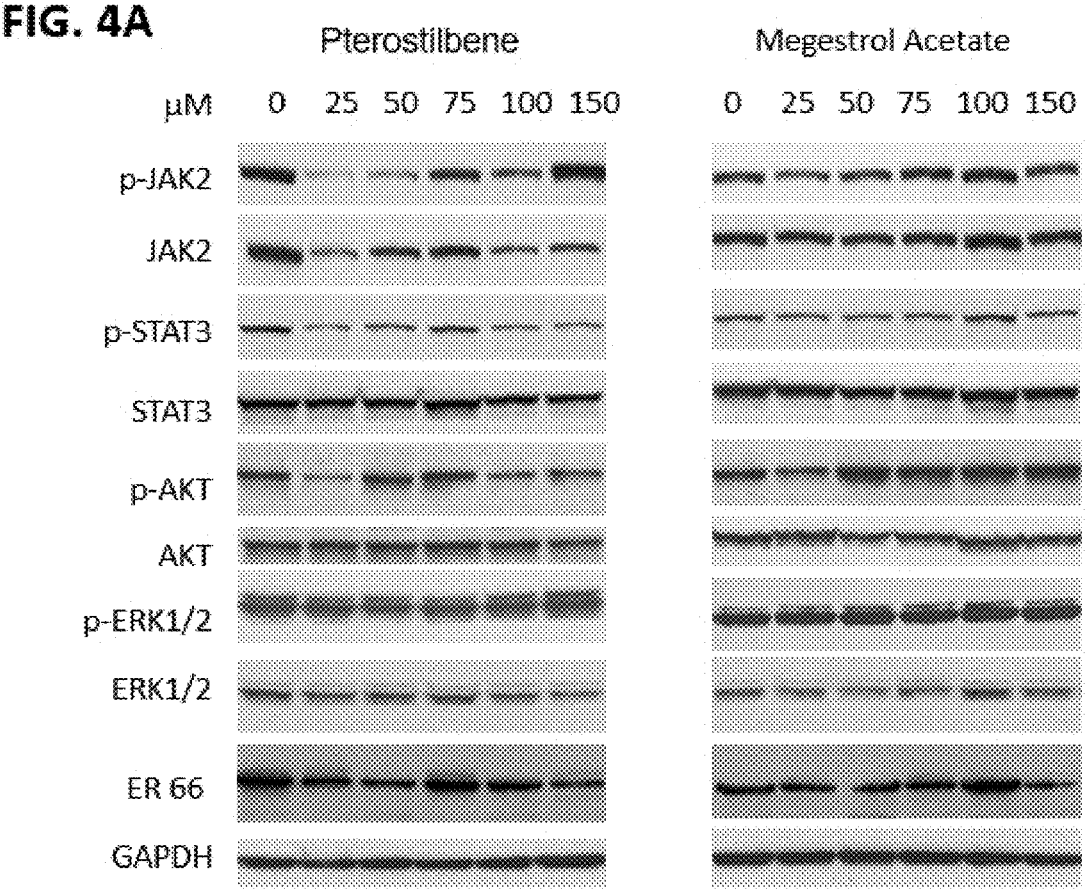
FIGS. 4A-4B. Effect of Pterostilbene (PTE) and megestrol acetate on the expression of cell signaling molecules.
Figure 4B:
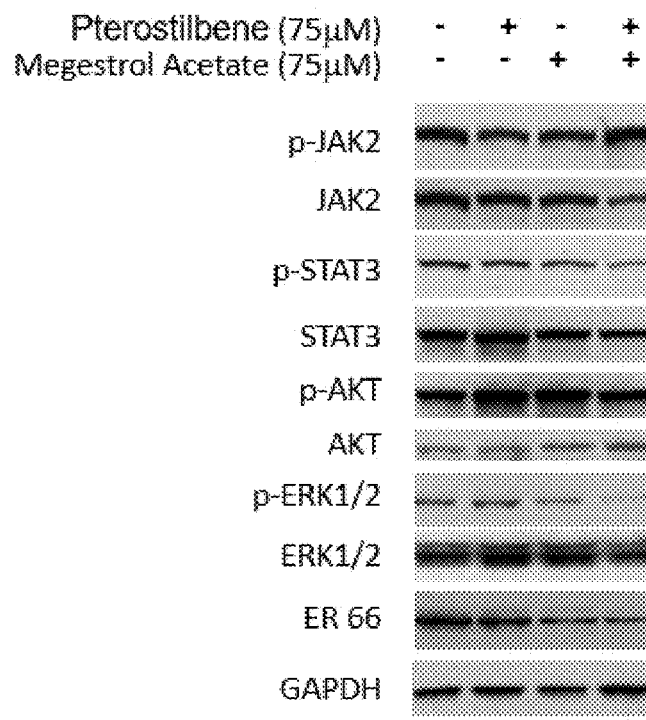

To understand the molecular mechanism underlying this synergistic effect, the molecular changes in the HEC-1A endometrial cancer cells in response to combination treatment of pterostilbene and megestrol acetate was investigated. A number of signaling pathways, including MAPK/ERK, PI3K/AKT and JAK/STAT3 pathways, are constitutively activated and play important roles in the growth and progression of endometrial cancer. To study the effect of pterostilbene and megestrol acetate on these signaling pathways, HEC-1A cells were treated with pterostilbene and megestrol acetate either alone or in combination for 24 hours, and tested for the expression of p-STAT3, p-AKT, p-ERK and ER-α by Western blot. As shown in FIG. 4B, the combination of pterostilbene with megestrol acetate caused an enhanced reduction of p-ERK1/2 and ER expression. When administered alone, neither agent significantly affected these pathways. Pterostilbene alone slightly decreased the expression of ER, but had no significant effect on the expression of p-STAT3, p-AKT and p-ERK1/2, while megestrol acetate alone did not significantly alter the expression of p-STAT3, p-AKT, p-ERK or ER (FIG. 4A). Taken together, the results demonstrated that dual treatment of pterostilbene and megestrol acetate can more effectively inhibit MAPK/ERK signaling pathway and led to an enhanced inhibition of cancer cell growth.

Pterostilbene in Combination with Megestrol Acetate Reduces Tumor Growth in an Endometrial Cancer Xenograft Mouse Model.

Figure 5A:
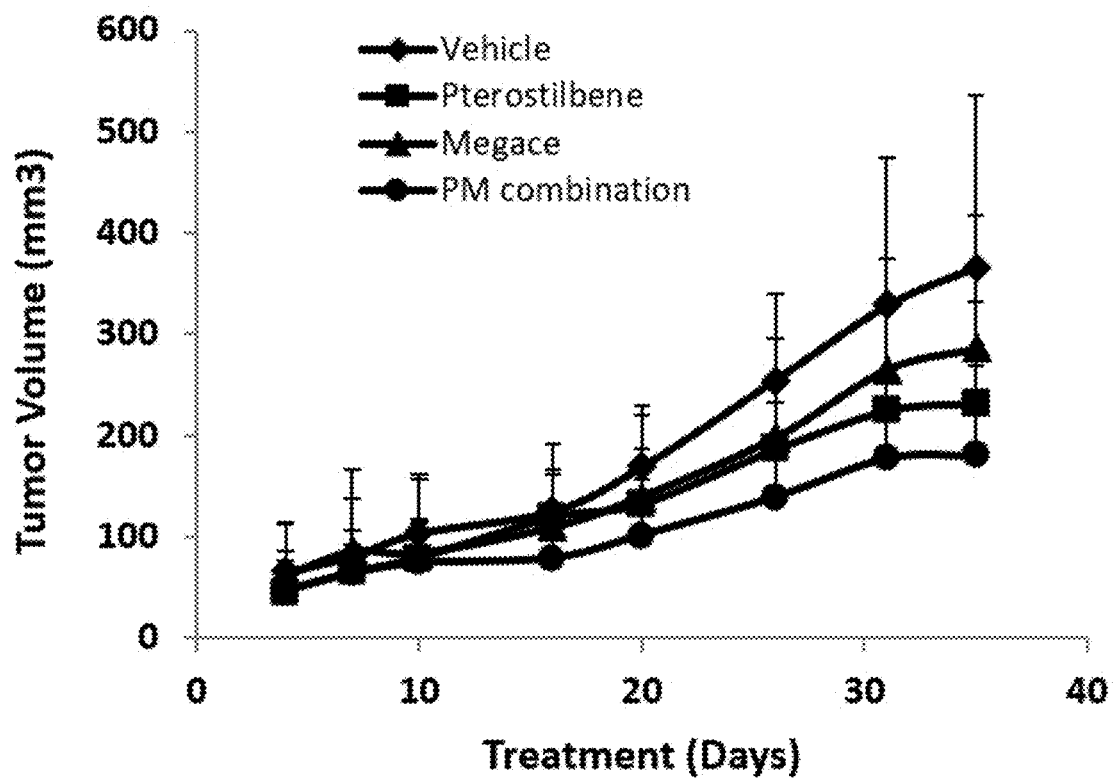
FIGS. 5A-5C. Anti-tumor activity of Pterostilbene (PTE) plus megestrol acetate ("Megace") in HEC-1A xenograft model. HEC-1A cells were implanted subcutaneously into the right flank of nude mice. Tumors were treated daily with vehicle, Pterostilbene (30 mg/kg), megestrol acetate (10 mg/kg) or combination of both. Tumor volume (FIG. 5A) and body weight (FIG. 5B) were measured once or twice a week.
Figure 5B:
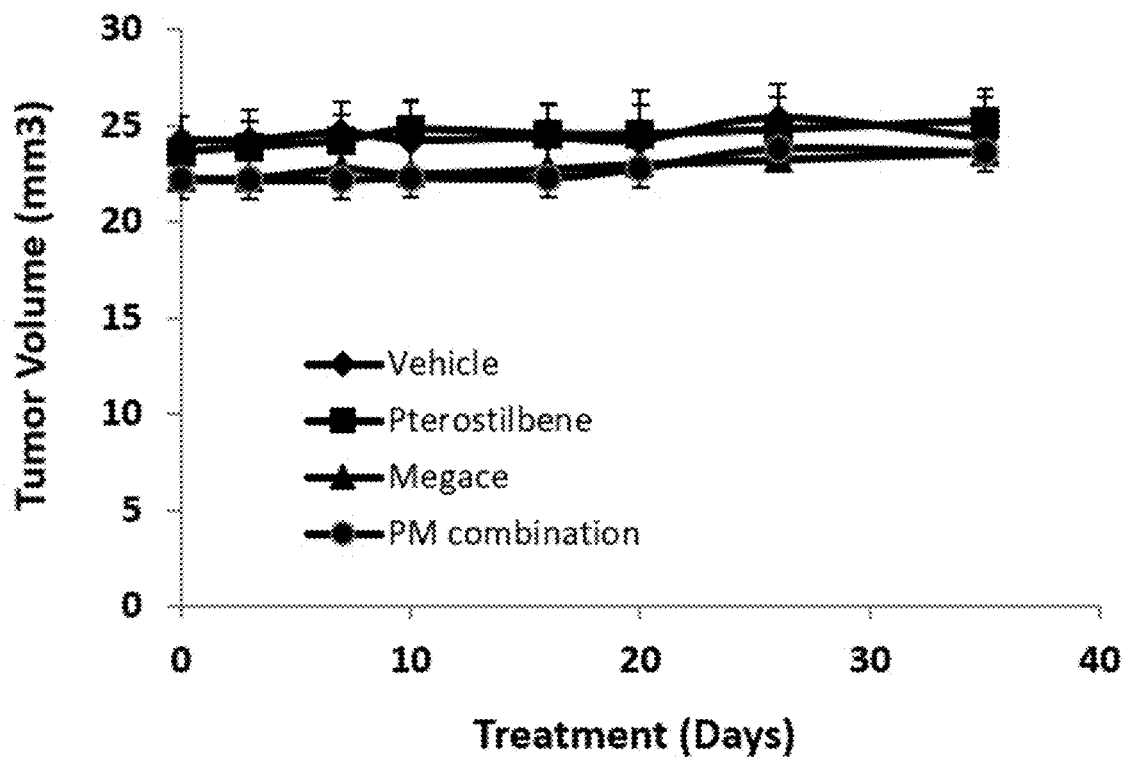
Figure 5C:
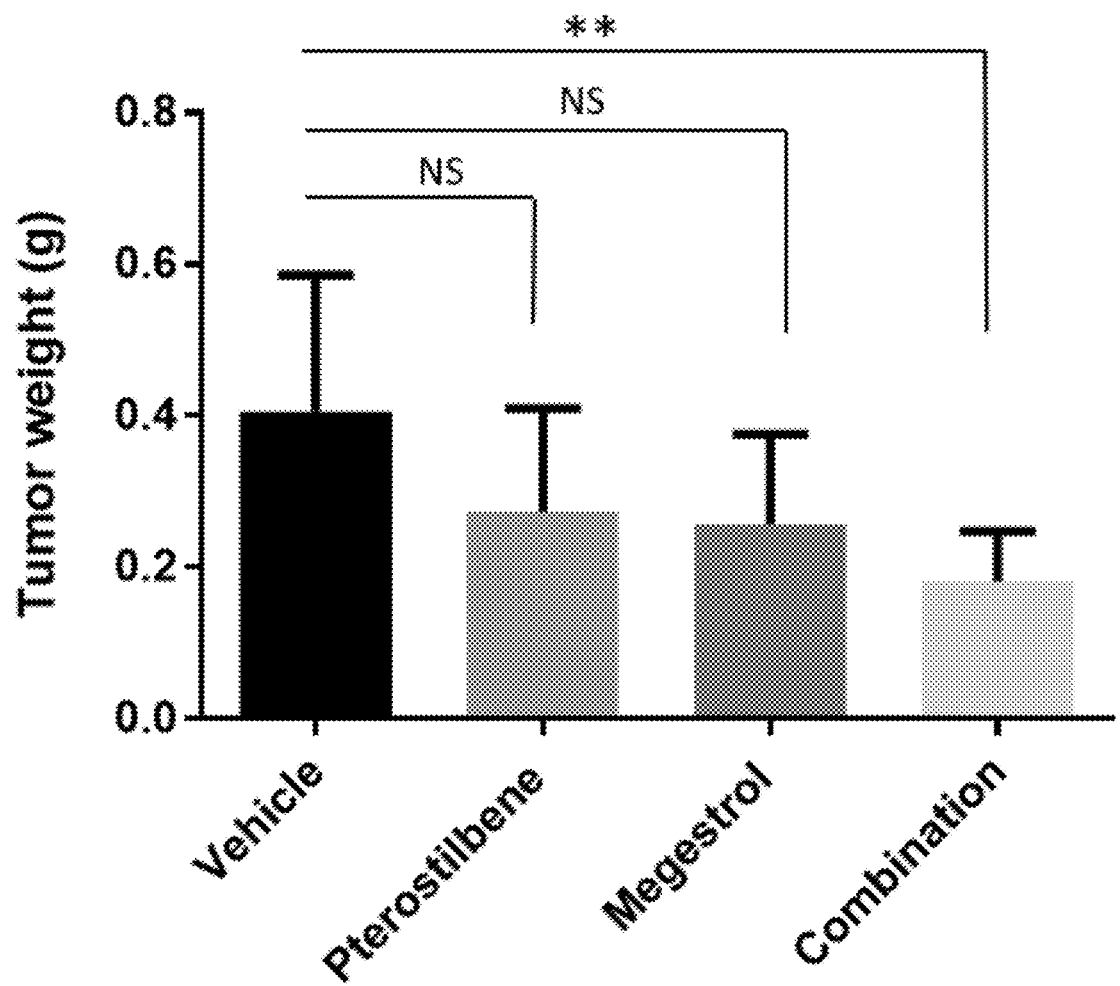

Anti-tumor activity of pterostilbene and/or megestrol acetate was evaluated in a HEC-1A xenograft mouse model (FIGS. 5A-5C). HEC-1A cells were implanted subcutaneously in the right flank of nude mice. When the tumors are palpable, mice were randomized into four groups and treated with vehicle control, pterostilbene, megestrol acetate and pterostilbene plus megestrol acetate via oral gavage. Tumor volume (FIG. 5A) and body weight (FIG. 5B) were monitored twice weekly, and tumor weight measured at the end of the treatment (5 weeks) (FIG. 5C). The combination of pterostilbene and megestrol acetate showed significant tumor growth reduction (both tumor volume and tumor weight), while the tumor growth reduction for pterostilbene or megestrol acetate alone were non-significant (FIG. 5A and FIG. 5C).

The Natural Stilbenoid Pterostilbene Synergizes the Antineoplastic Effects of Megestrol Acetate in Endometrial Cancer Few treatment options are available for patients with advanced stage and recurrent endometrial carcinoma. Novel therapies are difficult to establish in this patient population which tends to be older and plagued by comorbidities such as diabetes mellitus, morbid obesity, and hypertension. Therefore, novel, non-toxic therapies are urgently needed. In the current investigation, the therapeutic effect of the addition of the orally available, natural antioxidant, pterostilbene, to a well-established endometrial cancer therapy, megestrol acetate, was tested in endometrial cancer cells and a mouse model. The results demonstrate for the first time that dual treatment of pterostilbene and megestrol acetate results in a synergistic antiproliferative effect in endometrial cancer cells, and significantly reduces tumor growth in a xenograft endometrial cancer mouse model, as demonstrated by reduction in tumor weight and volume. Investigation into molecular mechanisms leading to this synergy reveals that the combination more effectively suppresses activation of the ERK1/2 pathway, as well as ER expression, but did not impact AKT or STAT3 activation.

The role of pterostilbene in induction of apoptosis and cell cycle arrest has been demonstrated in other cancers, including bladder, lung and gastric cancer[30-32]. These pro-apoptotic effects have been observed in numerous in vitro tumor cell lines, and include upregulation of proapoptotic mitochondrial derived proteins (Bax, Bak etc), while downregulating anti-apoptotic proteins Bcl-2 and Bcl-xl, and inducing the expression of caspase 3.[38] For example, in breast cancer, pterostilbene induces apoptosis and anti-proliferation in ER-α rich breast cancer cells, with additive effect by administration of tamoxifen[39,40]. In endometrial cancer cell lines, pterostilbene was recently demonstrated to induce cytotoxicity via caspase-dependent apoptosis, via down-regulation of miR-663b, and upregulation of BCL-G[41]. The investigation herein demonstrated that pterostilbene as a single treatment led to an increased cleavage of an apoptotic marker, caspase 3, and a decreased expression of cell survival proteins, BCL-2 and BCL-xl, in endometrial cells, similar to the pro-apoptotic effects by pterostilbene reported for other cancer cell lines. In addition, pterostilbene alone inhibited the expression of the cell cycle regulators, such as cyclin D1, cyclin B1 and CDK4. These activities were further enhanced when pterostilbene was combined with megestrol acetate, while megestrol acetate alone had little effect on apoptosis and cell cycle progression in endometrial cells.

The effect of pterostilbene on estrogen receptors (ER) in endometrial cancer has not yet been studied elsewhere. Its structural analogue, Resveratrol, has been shown to bind to both estrogen receptor alpha and beta[42-44]. Recently, both Resveratrol and pterostilbene have been shown to act as ER beta agonists in prostate cancer cells, through which they inhibit cell proliferation via induction of mitochondrial antioxidant enzymes[45]. Combination of Resveratrol and pterostilbene was also shown to restore ERalpha expression in triple negative breast cancer[46]. In colon cancer, pterostilbene suppressed AKT and ERK phosphorylation more effectively in ER-3 rich colon cancer cells, as opposed to ER-β poor cells[33]. While the majority of ERs are located in the nucleus and act as transcription factors, estrogen binding to membranous ERs leads to non-genomic processes which activate signal transduction pathways such as PI3K/AKT and MAPK/ERK pathways[47]. This non-genomic effect has previously been described in the endometrial cancer cell line, HEC-1A, where estradiol binding to ER induces ERK1/2 activation, but not AKT activation[36]. Similarly, the results disclosed herein show that in HEC-1A cells, the combination of pterostilbene and megestrol acetate suppresses ERK1/2 phosphorylation, but not AKT phosphorylation. Whether binding of pterostilbene to membrane-bound ERs reduces estrogen binding and therefore results in attenuation of the MAPK/ERK pathway is unknown, but may be hypothesized from the above studies. This study revealed mild reduction of ER expression by pterostilbene or megestrol acetate alone, however the combination of megestrol acetate and pterostilbene together significantly reduced ER expression in endometrial cancer cells. Conventionally speaking, progestins are not anti-estrogens, and only indirectly reduce ER expression via negative feedback. Despite decades of use, the exact mechanism of progestin therapy has not been elucidated in endometrial cancer, and has been attributed largely to the atrophy-inducing effect on the endometrium[16,48-50]. Nonetheless, lung metastases from endometrial cancer can occasionally be treated effectively with progestins. In this study, neither pterostilbene nor megestrol acetate alone substantially attenuated ERK signaling, though their combined effect on the attenuation of the ERK pathway points to an additive effect in enhanced antineoplastic activity. One could hypothesize that the combination of megestrol acetate and pterostilbene is synergistic in inhibiting important signaling pathways such as MAPK/ERK, by way of reduced ER expression via megestrol acetate, and ER binding by pterostilbene, but further studies are needed to confirm this.

The in vivo study demonstrates that dual treatment of pterostilbene and megestrol acetate results in significant tumor growth inhibition. The pterostilbene dose used for oral gavage of mice was 30 mg/kg, which is reported to be the equivalent of 5 times the mean human intake of pterostilbene (25 gm/day), or 125 mg/day for humans.[51] A recent clinical trial investigating the safety of pterostilbene concluded that pterostilbene is generally safe for use in humans up to 250 mg/day.[52] Similarly, the megestrol acetate dose used in our animal study (10 mg/kg), would favorably compare to human doses of up to 800 mg/day used for endometrial cancer patients.[13] Both pterostilbene and megestrol acetate are well tolerated in comparison to most cytotoxic treatments for endometrial cancer, and its synergistic in vivo activity to inhibit tumor growth is thus promising for endometrial cancer patients who frequently have a poor performance status.

This study shows that the dual treatment with pterostilbene and megestrol acetate can inhibit multiple cell growth and survival pathways and results in an enhanced inhibition of cancer cell growth. In embodiments, the combination of pterostilbene and megestrol acetate shows anti-tumor activity in endometrial cancer.

Materials and Methods

Reagents. Pterostilbene was kindly provided by Chromadex, Inc, Irvine, Calif. Megestrol acetate was from Selleck Chemicals, megestrol acetate suspension was obtained from Morton Grove Pharmaceuticals (Morton Grove, Ill.). Antibodies against p-ERK (T202/Y204), ERK, p-AKT (S473), BCL-2, Cyclin D, caspase 3, PARP, ER-66 and GAPDH were obtained from Cell Signaling Technology (Danvers, Mass.). The antibody against AKT was from Santa Cruz Biotechnology (Dallas, Tex.).

Cell Culture. Human endometrial cancer cell lines HEC-1A and ECC-1 cells were from American Type Culture Collection (Rockville, Md.). Both cell lines were cultured in RPMI-1640 medium, containing 10% FBS and 1% penicillin/streptomycin (P/S). All cells were grown in 5% (v/v) $CO_2$ at 37° C.

Cell viability assays. Cells (4000 per well) were plated in 96-well plate format in 100 μl growth medium. Cells were treated with DMSO or drugs the next day at the indicated concentrations and incubated for an additional 2-3 days. Viable cells were determined either by the MTS assay (Promega, Madison, Wis., USA) or the acid phosphatase assay[53,54]. For the MTS assay, 25 μl MTS solution was added directly into each well according to the manufacturer's instructions. For the acid phosphatase assay, all the media was removed and p-nitrophenyl phosphate substrate (10 mM 100 μl) was added into each well and incubated at 37° C. for 45 mins. NaOH was added to stop the reaction and the absorbance was read at 415 nM. The $IC_{50}$ was determined using the Calcusyn software (Biosoft, Ferguson, Mo.).

Determination of combination index (CI). The combination index (CI) was determined using the Chou-Talalay method[37] using the Calcusyn software (Biosoft, MO).

Western blot analysis. Western blots were performed as described previously[55,56] Cells were grown in complete medium overnight and treated with DMSO or drugs at various concentrations for 24 hrs. Cells were washed in cold PBS and lysed in RIPA lysis buffer (Thermo Scientific) containing Halt protease and phosphatase inhibitors (Thermo Scientific). Proteins were quantified using BCA protein assay reagent (Thermo Scientific). Equal amounts of protein were separated by SDS-polyacrylamide gel electrophoresis, transferred to polyvinylidene fluoride membranes and incubated with total and phosphorylated protein-specific antibodies. Binding of the primary antibody was detected using a horseradish peroxidase (HRP)-conjugated secondary antibody and chemiluminescent substrates (Thermo Scientific).

Animal models. All animal studies were carried out under protocols approved by the Institutional Animal Care and Use Committee (IACUC) at City of Hope in accordance with all applicable federal, state, and local requirements and institutional guidelines. HEC-1A cells ($2\times10^6$ in 100 μl) were inoculated subcutaneously into the right flank of 6- to 8-week-old female nude mice. Once the tumors were palpable, animals were randomized into groups of 10 to achieve an equal distribution of tumor sizes in all treatment groups. Mice were then treated by oral gavage daily with vehicle, Pterostilbene (30 mg/kg), megestrol acetate (10 mg/kg), or a combination of both agents. The doses for these two drugs were chosen based on previously published studies. Tumor volumes were assessed using calipers twice a week. Tumor volumes were determined using the formula (Width)$^2$× Length×0.52. Body weight was monitored weekly as an indicator of drug-induced toxicity and overall health of the mice.

Statistical analysis. Data are presented as mean±S.D. Student's t-test was used to compare the means of two groups. All the experiments were repeated 2 to 4 times. $P<0.05$ was considered statistically significant.

Pterostilbene in Combination with Megestrol Acetate Reduces Tumor Growth in Endometrial Cancer Pterostilbene (PTE) is a resveratrol analog with improved bioavailability, and known antitumor activity in several cancers. It acts by antiproliferative and apoptotic mechanisms to reduce tumor growth. The dietary supplement pterostilbene was tested in endometrial cancer cells and in an endometrial cancer mouse model with or without megestrol acetate (MA), a progestin hormone that is frequently used to treat endometrial cancer. The studies show significant reduction in proliferation of endometrial cancer cells following treatment with pterostilbene with or without megestrol acetate, compared to megestrol acetate alone. The combination of PTE and MA is synergistic in significantly reducing proliferation in several endometrial cancer cells. Additionally, markers for cell cycle and cell survival are downregulated by PTE with or without MA, and this combination increased the expression of apoptosis markers. In a xenograft endometrial cancer mouse model, the combination of PTE and MA significantly reduced tumor growth as compared to MA alone. These results present compelling proof for the anti-tumor activity of PTE, which in combination with MA, exceeds the effect of MA alone in endometrial cancer.

Megestrol acetate (and other progestins) has long been used as alternative or second-line treatment for endometrial cancer. In metastatic and recurrent endometrial cancer patients, the reported response rate of MA is 25-30%. MA is also used for fertility sparing treatment of young endometrial cancer and endometrial hyperplasia patients who desire to avoid a hysterectomy. The addition of a natural polyphenol with a low toxicity profile that could improve the effectiveness of MA would be specifically welcome in a cancer population that is often plagued by obesity and comorbidities, making it difficult to test novel drugs with significant side effects.

TABLE 1

Evaluation of synergistic interaction between PTE and Megestrol acetate in HEC-1A and ECC-1 cells.

| Cells | PTE:Megestrol acetate | Combination index (CI) ED50 | ED75 | ED90 | Fold reduction (IC50) PTE | Megestrol acetate |
|---|---|---|---|---|---|---|
| HEC-1A | 1:1 | 0.36 | 0.47 | 0.61 | 2.75 | >1000 |
| ECC-1 | 1:1 | 0.34 | 0.47 | 0.64 | 2.91 | >1000 |

TABLE 2

Evaluation of synergistic interaction between PTE and Megestrol acetate in variety of molar ratios on the viability of HEC-1A cells.

| PTE:Megestrol acetate | Combination Index (CI) ED50 | ED75 | ED90 | IC50 (μM) PTE | Megestrol acetate |
|---|---|---|---|---|---|
| 12:1 | 0.86 | 0.89 | 0.93 | 51.66 | 4.30 |
| 3:1 | 0.71 | 0.72 | 0.74 | 36.57 | 12.19 |
| 1:1 | 0.36 | 0.47 | 0.61 | 23.30 | 23.30 |
| 1:2 | 0.17 | 0.50 | 1.43 | 11.17 | 22.34 |
| 1:4 | 0.08 | 1.16 | 16.8 | 5.10 | 20.40 |

REFERENCES

1. Siegel, R. L., Miller, K. D. & Jemal, A. Cancer statistics, 2016. *CA: a cancer journal for clinicians* 66, 7-30, doi:10.3322/caac.21332 (2016).
2. Morice, P., Leary, A., Creutzberg, C., Abu-Rustum, N. & Darai, E. Endometrial cancer. *Lancet* 387, 1094-1108, doi:10.1016/S0140-6736(15)00130-0 (2016).
3. Dizon, D. S. & Birrer, M. J. Advances in the diagnosis and treatment of uterine sarcomas. *Discovery medicine* 17, 339-345 (2014).
4. Oza, A. M. et al. Phase II study of temsirolimus in women with recurrent or metastatic endometrial cancer: a trial of the NCIC Clinical Trials Group. *Journal of clinical oncology: official journal of the American Society of Clinical Oncology* 29, 3278-3285, doi:10.1200/JCO.2010.34.1578 (2011).
5. Aghajanian, C. et al. Phase II trial of bevacizumab in recurrent or persistent endometrial cancer: a Gynecologic Oncology Group study. *Journal of clinical oncology: official journal of the American Society of Clinical Oncology* 29, 2259-2265, doi:10.1200/JCO.2010.32.6397 (2011).
6. Burke, W. M. et al. Endometrial cancer: A review and current management strategies: Part II. *Gynecologic Oncology* 134, 393-402, doi:http://doi.org/10.1016/j.ygyno.2014.06.003 (2014).
7. Burke, W. M. et al. Endometrial cancer: A review and current management strategies: Part I. *Gynecologic*

8. Bradford, L. S., Rauh-Hain, J. A., Schorge, J., Birrer, M. J. & Dizon, D. S. Advances in the management of recurrent endometrial cancer. *American journal of clinical oncology* 38, 206-212, doi:10.1097/COC.0b013e31829a2974 (2015).
9. Lheureux, S. & Oza, A. M. Endometrial cancer-targeted therapies myth or reality? Review of current targeted treatments. *European Journal of Cancer* 59, 99-108, doi:https://doi.org/10.1016/j.ejca.2016.02.016 (2016).
10. Myers, A. P. et al. Tumor mutational analysis of GOG248, a phase II study of temsirolimus or temsirolimus and alternating megestrol acetate and tamoxifen for advanced endometrial cancer (EC): An NRG Oncology/Gynecologic Oncology Group study. *Gynecologic Oncology* 141, 43-48, doi:10.1016/j.ygyno.2016.02.025 (2016).
11. DeLeon, M. C., Ammakkanavar, N. R. & Matei, D. Adjuvant therapy for endometrial cancer. *Journal of Gynecologic Oncology* 25, 136-147, doi:10.3802/jgo.2014.25.2.136 (2014).
12. Hansen, J. et al. The effect of weight-based chemotherapy dosing in a cohort of gynecologic oncology patients. *Gynecologic Oncology* 138, 154-158, doi:https://doi.org/10.1016/j.ygyno.2015.04.040 (2015).
13. Lentz, S. S., Brady, M. F., Major, F. J., Reid, G. C. & Soper, J. T. High-dose megestrol acetate in advanced or recurrent endometrial carcinoma: a Gynecologic Oncology Group Study. *Journal of clinical oncology: official journal of the American Society of Clinical Oncology* 14, 357-361, doi:10.1200/jco.1996.14.2.357 (1996).
14. Rauh-Hain, J. A. & del Carmen, M. G. Treatment for Advanced and Recurrent Endometrial Carcinoma: Combined Modalities. *The Oncologist* 15, 852-861, doi:10.1634/theoncologist.2010-0091 (2010).
15. Lee, W. L. et al. Hormone therapy for patients with advanced or recurrent endometrial cancer. *Journal of the Chinese Medical Association: JCMA* 77, 221-226, doi:10.1016/j.jcma.2014.02.007 (2014).
16. Yang, S., Thiel, K. W., De Geest, K. & Leslie, K. K. Endometrial cancer: reviving progesterone therapy in the molecular age. *Discovery medicine* 12, 205-212 (2011).
17. Kong, Y. et al. Pterostilbene induces apoptosis and cell cycle arrest in diffuse large B-cell lymphoma cells. *Scientific reports* 6, 37417, doi:10.1038/srep37417 (2016).
18. Lee, H., Kim, Y., Jeong, J. H., Ryu, J.-H. & Kim, W.-Y. ATM/CHK/p53 Pathway Dependent Chemopreventive and Therapeutic Activity on Lung Cancer by Pterostilbene. *PLoS ONE* 11, e0162335, doi:10.1371/journal.pone.0162335 (2016).
19. Dhar, S. et al. Dietary pterostilbene is a novel MTA1-targeted chemopreventive and therapeutic agent in prostate cancer. *Oncotarget* 7, 18469-18484, doi:10.18632/oncotarget.7841 (2016).
20. Nikhil, K., Sharan, S., Singh, A. K., Chakraborty, A. & Roy, P. Anticancer Activities of Pterostilbene-Isothiocyanate Conjugate in Breast Cancer Cells: Involvement of PPARγ. *PLoS ONE* 9, e104592, doi:10.1371/journal.pone.0104592 (2014).
21. Li, K. et al. Pterostilbene Acts through Metastasis-Associated Protein 1 to Inhibit Tumor Growth, Progression and Metastasis in Prostate Cancer. *PLoS ONE* 8, e57542, doi:10.1371/journal.pone.0057542 (2013).
22. Paul, S. et al. Anti-inflammatory action of pterostilbene is mediated through the p38 MAPK pathway in colon cancer cells. *Cancer prevention research* (Philadelphia, Pa.) 2, 650-657, doi:10.1158/1940-6207.capr-08-0224 (2009).
23. Pan, M.-H. et al. Pterostilbene inhibited tumor invasion via suppressing multiple signal transduction pathways in human hepatocellular carcinoma cells. *Carcinogenesis* 30, 1234-1242, doi:10.1093/carcin/bgp121 (2009).
24. Suh, N. et al. Pterostilbene, an Active Constituent of Blueberries, Suppresses Aberrant Crypt Foci Formation in the Azoxymethane-Induced Colon Carcinogenesis Model in Rats. *Clinical Cancer Research* 13, 350 (2007).
25. Hsiao, P. C. et al. Pterostilbene simultaneously induced G0/G1-phase arrest and MAPK-mediated mitochondrial-derived apoptosis in human acute myeloid leukemia cell lines. *PLoS ONE* 9, e105342, doi:10.1371/journal.pone.0105342 (2014).
26. Priego, S. et al. Natural polyphenols facilitate elimination of HT-29 colorectal cancer xenografts by chemoradiotherapy: a Bcl-2- and superoxide dismutase 2-dependent mechanism. *Molecular Cancer Therapeutics* 7, 3330-3342, doi:10.1158/1535-7163.mct-08-0363 (2008).
27. Xie, B. et al. Pterostilbene Inhibits Human Multiple Myeloma Cells via ERK1/2 and JNK Pathway In Vitro and In Vivo. *International Journal of Molecular Sciences* 17, 1927, doi:10.3390/ijms17111927 (2016).
28. Schmidt, L. et al. Case-specific potentiation of glioblastoma drugs by pterostilbene. *Oncotarget* 7, 73200-73215, doi:10.18632/oncotarget.12298 (2016).
29. Estrela, J. M., Ortega, A., Mena, S., Rodriguez, M. L. & Asensi, M. Pterostilbene: Biomedical applications. *Critical reviews in clinical laboratory sciences* 50, 65-78, doi:10.3109/10408363.2013.805182 (2013).
30. Pan, C. et al. Estrogen receptor-alpha36 is involved in pterostilbene-induced apoptosis and anti-proliferation in in vitro and in vivo breast cancer. *PloS one* 9, e104459, doi:10.1371/journal.pone.0104459 (2014).
31. Chen, R. J., Ho, C. T. & Wang, Y. J. Pterostilbene induces autophagy and apoptosis in sensitive and chemoresistant human bladder cancer cells. *Molecular nutrition & food research* 54, 1819-1832, doi:10.1002/mnfr.201000067 (2010).
32. Schneider, J. G., Alosi, J. A., McDonald, D. E. & McFadden, D. W. Pterostilbene inhibits lung cancer through induction of apoptosis. *The Journal of surgical research* 161, 18-22, doi:10.1016/j.jss.2009.06.027 (2010).
33. Tolba, M. F. & Abdel-Rahman, S. Z. Pterostilbine, an active component of blueberries, sensitizes colon cancer cells to 5-fluorouracil cytotoxicity. *Scientific reports* 5, 15239, doi:10.1038/srep15239 (2015).
34. Kuramoto, H. Studies of the growth and cytogenetic properties of human endometrial adenocarcinoma in culture and its development into an established line. *Acta obstetrica et gynaecologica Japonica* 19, 47-58 (1972).
35. Mo, B. et al. ECC-1 cells: a well-differentiated steroid-responsive endometrial cell line with characteristics of luminal epithelium. *Biology of reproduction* 75, 387-394, doi:10.1095/biolreprod.106.051870 (2006).
36. Zhang, L. et al. Nongenomic effect of estrogen on the MAPK signaling pathway and calcium influx in endometrial carcinoma cells. *J Cell Biochem* 106, 553-562, doi:10.1002/jcb.22017 (2009).
37. Chou, T. C. Drug combination studies and their synergy quantification using the Chou-Talalay method. *Cancer research* 70, 440-446, doi:10.1158/0008-5472.CAN-09-1947 (2010).

38. Kosuru, R., Rai, U., Prakash, S., Singh, A. & Singh, S. Promising therapeutic potential of pterostilbene and its mechanistic insight based on preclinical evidence. *European journal of pharmacology* 789, 229-243, doi:10.1016/j.ejphar.2016.07.046 (2016).

39. Mannal, P., McDonald, D. & McFadden, D. Pterostilbene and tamoxifen show an additive effect against breast cancer in vitro. *American journal of surgery* 200, 577-580, doi:10.1016/j.amjsurg.2010.07.022 (2010).

40. Mannal, P. W., Alosi, J. A., Schneider, J. G., McDonald, D. E. & McFadden, D. W. Pterostilbene inhibits pancreatic cancer in vitro. *Journal of gastrointestinal surgery: official journal of the Society for Surgery of the Alimentary Tract* 14, 873-879, doi:10.1007/s11605-010-1164-4 (2010).

41. Wang, Y. L. et al. Pterostilbene suppresses human endometrial cancer cells in vitro by down-regulating miR-663b. *Acta pharmacologica Sinica*, doi:10.1038/aps.2017.60 (2017).

42. Gehm, B. D., McAndrews, J. M., Chien, P. Y. & Jameson, J. L. Resveratrol, a polyphenolic compound found in grapes and wine, is an agonist for the estrogen receptor. *Proceedings of the National Academy of Sciences of the United States of America* 94, 14138-14143 (1997).

43. Bowers, J. L., Tyulmenkov, V. V., Jernigan, S. C. & Klinge, C. M. Resveratrol acts as a mixed agonist/antagonist for estrogen receptors alpha and beta. *Endocrinology* 141, 3657-3667, doi:10.1210/endo.141.10.7721 (2000).

44. Bhat, K. P. et al. Estrogenic and antiestrogenic properties of resveratrol in mammary tumor models. *Cancer Res* 61, 7456-7463 (2001).

45. Robb, E. L. & Stuart, J. A. The stilbenes resveratrol, pterostilbene and piceid affect growth and stress resistance in mammalian cells via a mechanism requiring estrogen receptor beta and the induction of Mn-superoxide dismutase. *Phytochemistry* 98, 164-173, doi:10.1016/j.phytochem.2013.11.019 (2014).

46. Kala, R. & Tollefsbol, T. O. A Novel Combinatorial Epigenetic Therapy Using Resveratrol and Pterostilbene for Restoring Estrogen Receptor-α (ERα) Expression in ERα-Negative Breast Cancer Cells. *PLoS ONE* 11, e0155057, doi:10.1371/journal.pone.0155057 (2016).

47. Bjornstrom, L. & Sjoberg, M. Estrogen receptor-dependent activation of AP-1 via non-genomic signalling. *Nuclear receptor* 2, 3, doi:10.1186/1478-1336-2-3 (2004).

48. Kim, J. J., Kurita, T. & Bulun, S. E. Progesterone Action in Endometrial Cancer, Endometriosis, Uterine Fibroids, and Breast Cancer. *Endocrine Reviews* 34, 130-162, doi:10.1210/er.2012-1043 (2013).

49. Dai, D., Wolf, D. M., Litman, E. S., White, M. J. & Leslie, K. K. Progesterone Inhibits Human Endometrial Cancer Cell Growth and Invasiveness. *Cancer Research* 62, 881 (2002).

50. Zhang, K. & Chow, P. K. The effect of megestrol acetate on growth of HepG2 cells in vitro and in vivo. *Clin Cancer Res* 10, 5226-5232, doi:10.1158/1078-0432.CCR-04-0061 (2004).

51. Ruiz, M. J. et al. Dietary administration of high doses of pterostilbene and quercetin to mice is not toxic. *Journal of agricultural and food chemistry* 57, 3180-3186, doi:10.1021/jf803579e (2009).

52. Riche, D. M. et al. Analysis of safety from a human clinical trial with pterostilbene. *Journal of toxicology* 2013, 463595, doi:10.1155/2013/463595 (2013).

53. Yang, T. T., Sinai, P. & Kain, S. R. An acid phosphatase assay for quantifying the growth of adherent and nonadherent cells. *Analytical biochemistry* 241, 103-108, doi:10.1006/abio.1996.0383 (1996).

54. Wen, W. et al. Synergistic anti-tumor effect of combined inhibition of EGFR and JAK/STAT3 pathways in human ovarian cancer. *Molecular cancer* 14, 100, doi:10.1186/s12943-015-0366-5 (2015).

55. Wen, W. et al. Targeting JAK1/STAT3 signaling suppresses tumor progression and metastasis in a peritoneal model of human ovarian cancer. *Molecular cancer therapeutics* 13, 3037-3048, doi:10.1158/1535-7163.MCT-14-0077 (2014).

56. Lu, J. et al. Novel angiogenesis inhibitory activity in cinnamon extract blocks VEGFR2 kinase and downstream signaling. *Carcinogenesis* 31, 481-488, doi:10.1093/carcin/bgp292 (2010).

What is claimed is:

1. A method of treating endometrial cancer in a subject in need thereof, the method comprising administering to the subject a combined synergistic amount of (i) pterostilbene or a pharmaceutically acceptable salt thereof; and (ii) megestrol acetate or a pharmaceutically acceptable salt thereof,
   and wherein no other active agent that is used to kill or inhibit the proliferation of cancer cells is administered to the subject.

2. The method of claim 1, wherein the pterostilbene is administered at a dose of less than 50 mg, administered once per day, administered orally, or a combination thereof.

3. The method of claim 1, wherein the megestrol acetate is administered at a dose of 40 mg to 320 mg.

4. The method of claim 1, wherein the megestrol acetate is administered at a dose of less than 40 mg, administered once per day, administered orally, or a combination thereof.

5. The method of claim 1, wherein the pterostilbene or pharmaceutically acceptable salt thereof and the megestrol acetate or pharmaceutically acceptable salt thereof are administered to the subject in a single pharmaceutical composition.

6. The method of claim 1, wherein treating the subject comprises reducing the volume of a tumor in the subject.

7. The method of claim 1, wherein the subject is obese, post-menopausal, or pre-menopausal.

8. The method of claim 1, wherein the subject has been (a) previously administered tamoxifen, (b) previously administered radiotherapy to the pelvis, (c) diagnosed with ovarian cancer, (d) diagnosed with an ovarian granulosa cell tumor or a thecoma, (e) previously administered a chemotherapeutic agent other than megestrol acetate or pterostilbene, (f) previously administered a taxane, an anthracycline, or a platin, or (g) previously administered hydroxyprogesterone caproate, letrozole, or medroxyprogesterone.

9. The method of claim 1, wherein the subject has a mutation in or altered expression of a ARID1A, CTNNB1, FGFR2, KRAS, PIK3R1, TP53, PTEN, PPP2R1A, PIK3CA, PIK3R1, STK15, CCNE1, ERBB2, or CCND1 gene.

10. The method of claim 1, wherein the subject has reduced expression of a MLH1, RASSF1A, SPRY2, or CDKN2A gene.

11. The method of claim 1, wherein the endometrial cancer: (a) is Type I or Type II endometrial cancer; (b) is a carcinoma, an adenocarcinoma, a carcinosarcoma, or a mesenchymal tumor; (c) has a mucinous histology, a mixed histology or a undifferentiated histology, (d) is endometroid, serous, or clear-cell endometrial cancer; (e) is an endometrioid adenocarcinoma, an endometrioid carcinoma, a serous carcinoma, a clear cell carcinoma, a mucinous carcinoma, a mixed or undifferentiated carcinoma, a squamous cell carcinoma, a transitional cell carcinoma, or a endometrial stromal sarcoma, (f) is recurrent endometrial cancer, or (g) is Stage 0, Stage IA, IB, II, IIA, IIIA, IIIB, IIIC1, IIIC2, IVA or IVB endometrial cancer.

12. The method of claim 1, wherein the subject: (a) has not received a hysterectomy; (b) has not been previously administered radiation therapy or a chemotherapeutic agent; (c) has not been previously administered pterostilbene; or (d) has not been previously administered megestrol acetate.

13. The method of claim 1, wherein the subject has previously been administered: (a) megestrol acetate without pterostilbene, or (b) pterostilbene without megestrol acetate.

14. The method of claim 8, wherein the subject has previously been administered paclitaxel, docetaxel, doxorubicin, cisplatin, carboplatin, liposomal doxorubicin, bevacizumab, temsirolimus, ifosfamide, or topotecan.

15. The method of claim 1, wherein the subject has a tumor, wherein the subject has been administered megestrol acetate, and wherein the volume of the tumor has not decreased since the subject was administered megestrol acetate.

16. The method of claim 1, wherein the subject has a tumor, wherein the subject has been administered pterostilbene, and wherein the volume of the tumor has not decreased since the subject was administered pterostilbene.

17. The method of claim 1, wherein the subject has previously received a first amount of megestrol acetate, and further wherein the therapeutically effective amount comprises megestrol acetate in an amount less than said first amount.

18. The method of claim 1, wherein the subject has previously received a first amount of pterostilbene, and further wherein the therapeutically effective amount comprises pterostilbene or a pharmaceutically acceptable salt thereof in an amount that is less than said first amount.

* * * * *